US010685088B2

(12) United States Patent
Ohashi et al.

(10) Patent No.: US 10,685,088 B2
(45) Date of Patent: Jun. 16, 2020

(54) CONSOLE DEVICE OF PORTABLE TYPE, CONTROL METHOD AND RADIOGRAPHIC IMAGING SYSTEM

(71) Applicant: FUJIFILM Corporation, Tokyo (JP)

(72) Inventors: Yousuke Ohashi, Kanagawa (JP); Kiyohisa Okusu, Kanagawa (JP); Yuki Okabe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 992 days.

(21) Appl. No.: 14/854,044

(22) Filed: Sep. 15, 2015

(65) Prior Publication Data

US 2016/0078596 A1    Mar. 17, 2016

(30) Foreign Application Priority Data

Sep. 16, 2014   (JP) ................. 2014-187305

(51) Int. Cl.
*G06F 19/00*          (2018.01)
*A61B 6/00*           (2006.01)
(Continued)

(52) U.S. Cl.
CPC ............ *G06F 19/321* (2013.01); *A61B 6/463* (2013.01); *A61B 6/467* (2013.01); *A61B 6/508* (2013.01);
(Continued)

(58) Field of Classification Search
CPC ....... G06F 19/321; G06F 19/00; A61B 6/463; A61B 6/467; A61B 6/566; G16H 30/00
See application file for complete search history.

(56) References Cited

U.S. PATENT DOCUMENTS 6,469,717 B1 * 10/2002 Wineke ............... G06F 3/04845
                                                              715/765
6,993,114 B2 *  1/2006 Takasawa ............. G16H 15/00
                                                              378/98.5
(Continued)

FOREIGN PATENT DOCUMENTS

JP      2000-210266      8/2000
JP      2003-290150      10/2003
(Continued)

OTHER PUBLICATIONS

"Final Office Action of Japan Counterpart Application" with English translation thereof, dated May 24, 2017, p. 1-p. 4.
(Continued)

*Primary Examiner* — David J Makiya
*Assistant Examiner* — Soorena Kefayati
(74) *Attorney, Agent, or Firm* — JCIPRNET

(57) ABSTRACT

A radiographic imaging system includes a radiographic imaging device for creating a radiation image of a body. A console device of a portable type acquires the radiation image. The console device includes a display controller for performing display processing to display the radiation image in a user page on a display unit. The display controller performs display processing to display at least one optical image of the body in the user page on the display unit in a larger size than the radiation image. Preferably, the display unit includes a touchscreen display unit having a longer side equal to or less than 260 mm and a shorter side equal to or less than 180 mm, in a form of a tablet terminal device.

18 Claims, 30 Drawing Sheets

(51) Int. Cl.
*G16H 30/40* (2018.01)
*G16H 30/20* (2018.01)

(52) U.S. Cl.
CPC .......... *A61B 6/566* (2013.01); *G16H 30/20* (2018.01); *G16H 30/40* (2018.01)

(56) References Cited

U.S. PATENT DOCUMENTS

| | | | |
|---|---|---|---|
| 8,654,925 B2* | 2/2014 | Nishino | A61B 6/4405 378/115 |
| 8,976,931 B2* | 3/2015 | Lalena | A61B 6/4405 378/98.5 |
| 9,324,188 B1* | 4/2016 | Fram | G06T 19/00 |
| 9,398,887 B2* | 7/2016 | Miyazawa | G16H 40/63 |
| 9,405,183 B2* | 8/2016 | Ando | A61B 6/4266 |
| 9,642,588 B2* | 5/2017 | Goto | A61B 6/542 |
| 9,665,254 B2* | 5/2017 | Hayashi | G06F 3/04817 |
| 2003/0095697 A1* | 5/2003 | Wood | A61B 6/032 382/131 |
| 2004/0017894 A1* | 1/2004 | Takasawa | G16H 15/00 378/116 |
| 2005/0259116 A1* | 11/2005 | Araoka | A61B 6/463 345/619 |
| 2007/0237375 A1* | 10/2007 | Yamagishi | G06F 19/321 382/128 |
| 2008/0317206 A1* | 12/2008 | Yoshino | A61B 6/00 378/98 |
| 2010/0272343 A1* | 10/2010 | Abe | G06F 19/321 382/132 |
| 2011/0126127 A1* | 5/2011 | Mariotti | H04M 7/0027 715/753 |
| 2011/0301441 A1* | 12/2011 | Bandic | A61B 5/0059 600/306 |
| 2011/0311026 A1* | 12/2011 | Lalena | A61B 6/4405 378/98.5 |
| 2012/0051521 A1* | 3/2012 | Nishino | A61B 6/4405 378/98.5 |
| 2013/0012813 A1* | 1/2013 | Sakaguchi | A61B 6/12 600/431 |
| 2013/0088512 A1* | 4/2013 | Suzuki | A61B 6/463 345/629 |
| 2013/0121468 A1* | 5/2013 | Ohta | A61B 6/4405 378/63 |
| 2013/0177222 A1* | 7/2013 | Tridandapani | A61B 5/117 382/128 |
| 2013/0298082 A1* | 11/2013 | Soffer | G06F 3/0482 715/835 |
| 2013/0342668 A1* | 12/2013 | Kasumi | H04N 5/772 348/74 |
| 2014/0133721 A1* | 5/2014 | Fen | G16H 30/40 382/131 |
| 2014/0164968 A1* | 6/2014 | Aalami | G06F 19/321 715/771 |
| 2014/0187856 A1* | 7/2014 | Holoien | A61B 1/045 600/103 |
| 2014/0342301 A1* | 11/2014 | Fleer | G06T 15/08 433/27 |
| 2015/0046184 A1* | 2/2015 | Cocco | G16H 10/60 705/3 |
| 2015/0085066 A1* | 3/2015 | Desai | A61B 6/548 348/14.08 |
| 2015/0160844 A1* | 6/2015 | Kim | A61B 8/463 715/798 |
| 2015/0181629 A1* | 6/2015 | Jun | G06F 19/3418 455/420 |
| 2015/0317452 A1* | 11/2015 | Kozuka | G06F 16/5866 705/2 |
| 2015/0356271 A1* | 12/2015 | Kozuka | G06F 16/5838 705/2 |
| 2016/0213347 A1* | 7/2016 | Kawanishi | A61B 6/4464 |
| 2016/0217254 A1* | 7/2016 | Douglass | G06F 19/321 |

FOREIGN PATENT DOCUMENTS

| | | |
|---|---|---|
| JP | 2005-204861 | 8/2005 |
| JP | 2009089723 | 4/2009 |
| JP | 2010-125120 | 6/2010 |
| JP | 2011-160913 | 8/2011 |
| JP | 2012-029889 | 2/2012 |
| JP | 2014-064775 | 4/2014 |

OTHER PUBLICATIONS

"Office Action of Japan Counterpart Application", dated Nov. 9, 2016, p. 1-p. 13, with English translation thereof.

* cited by examiner

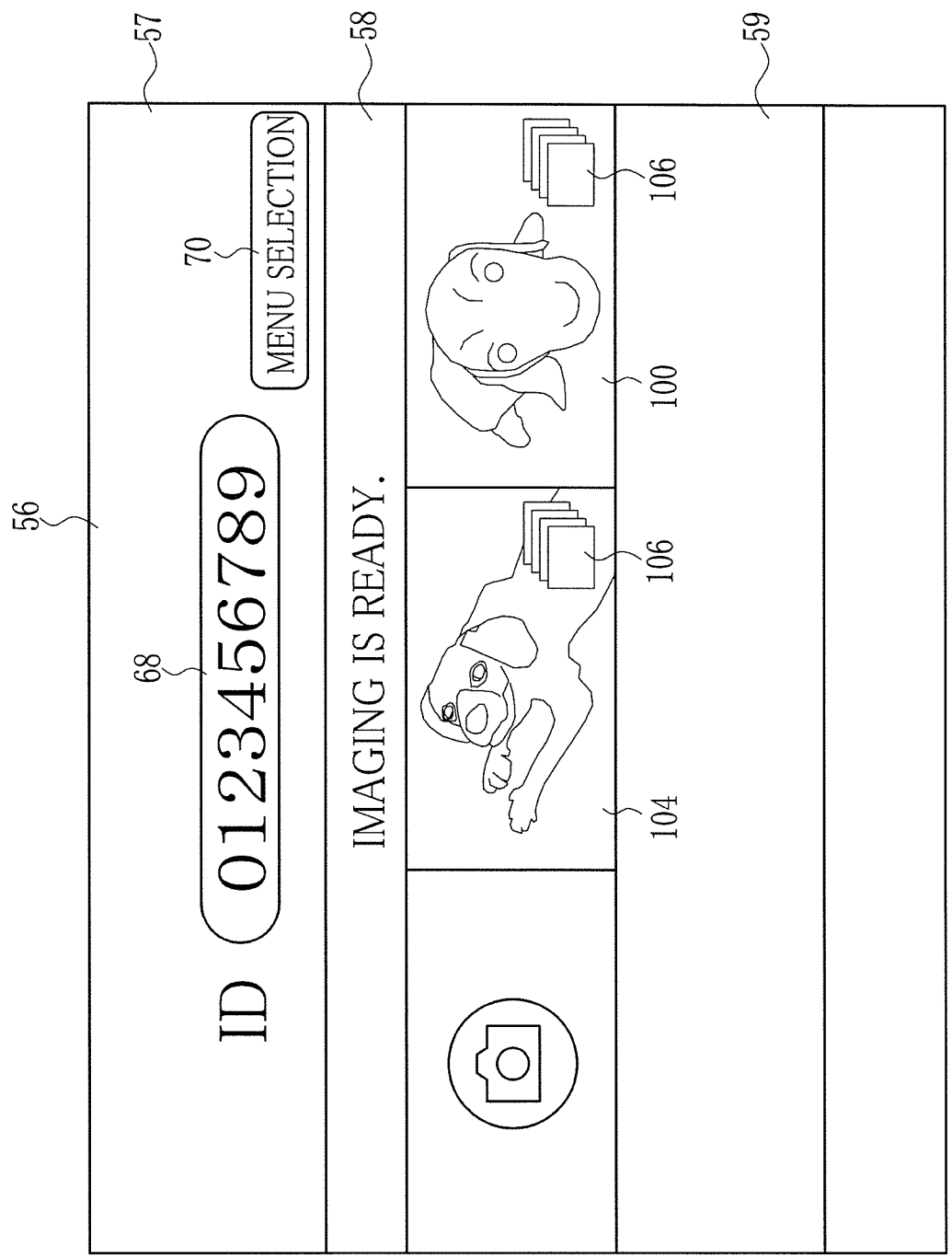

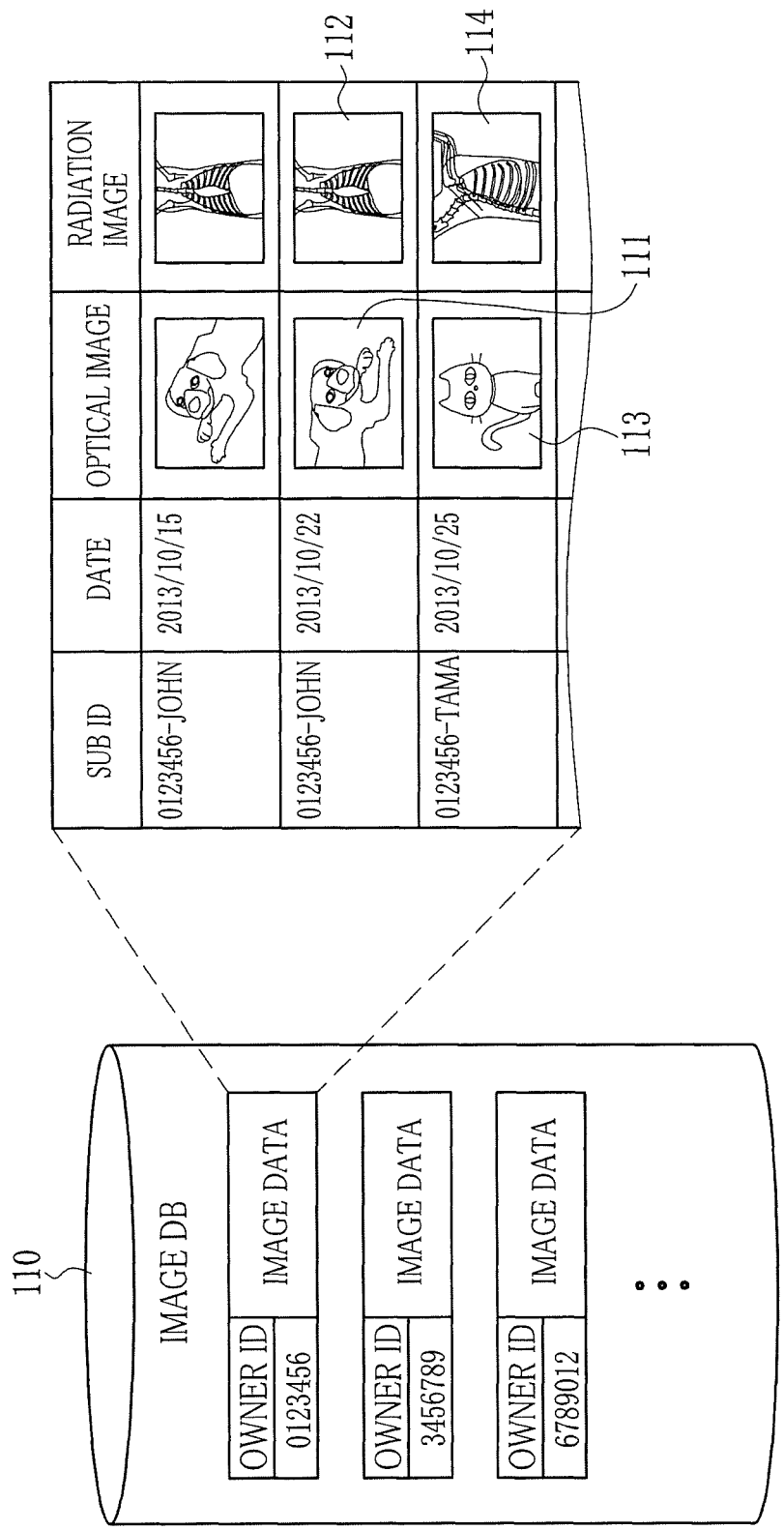

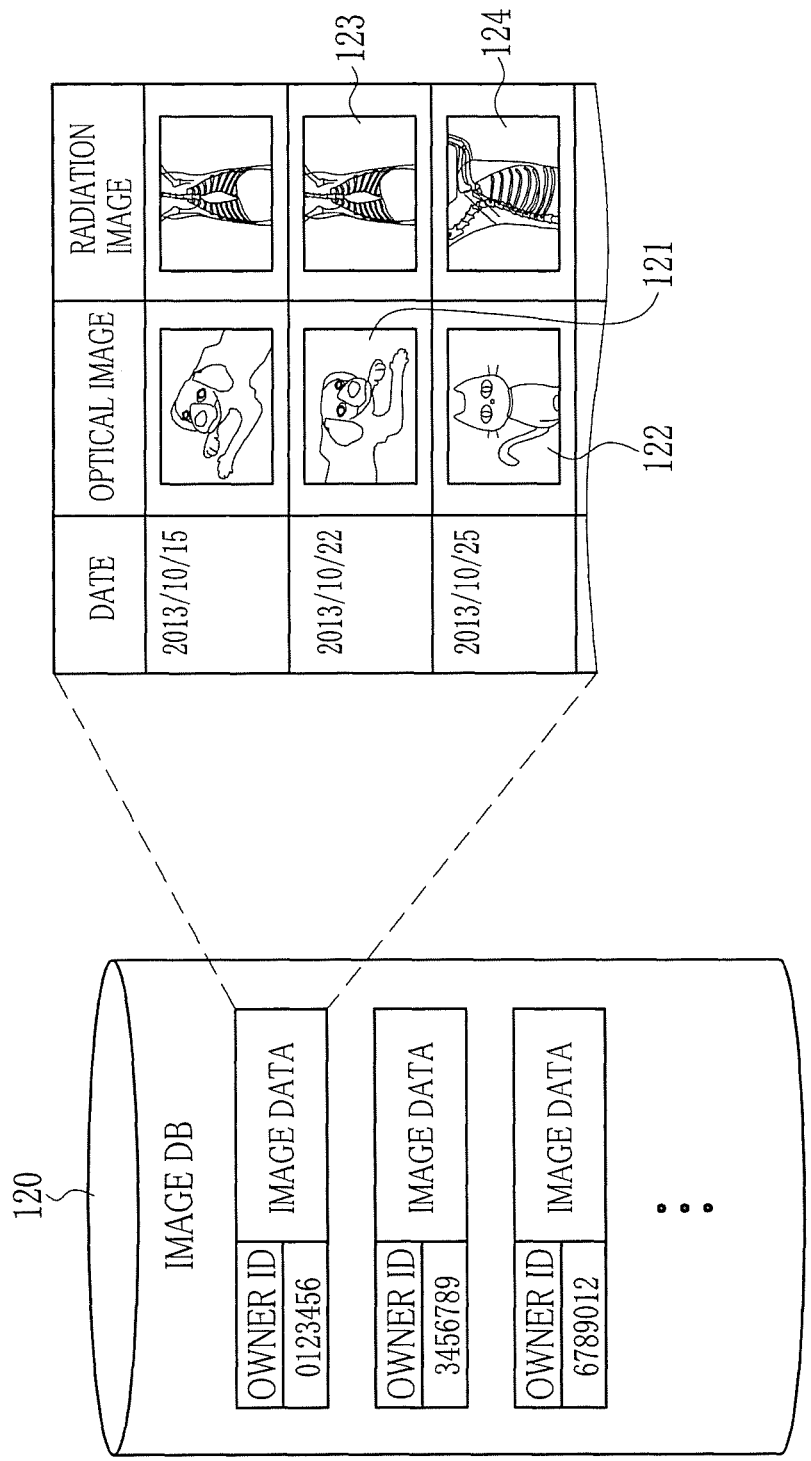

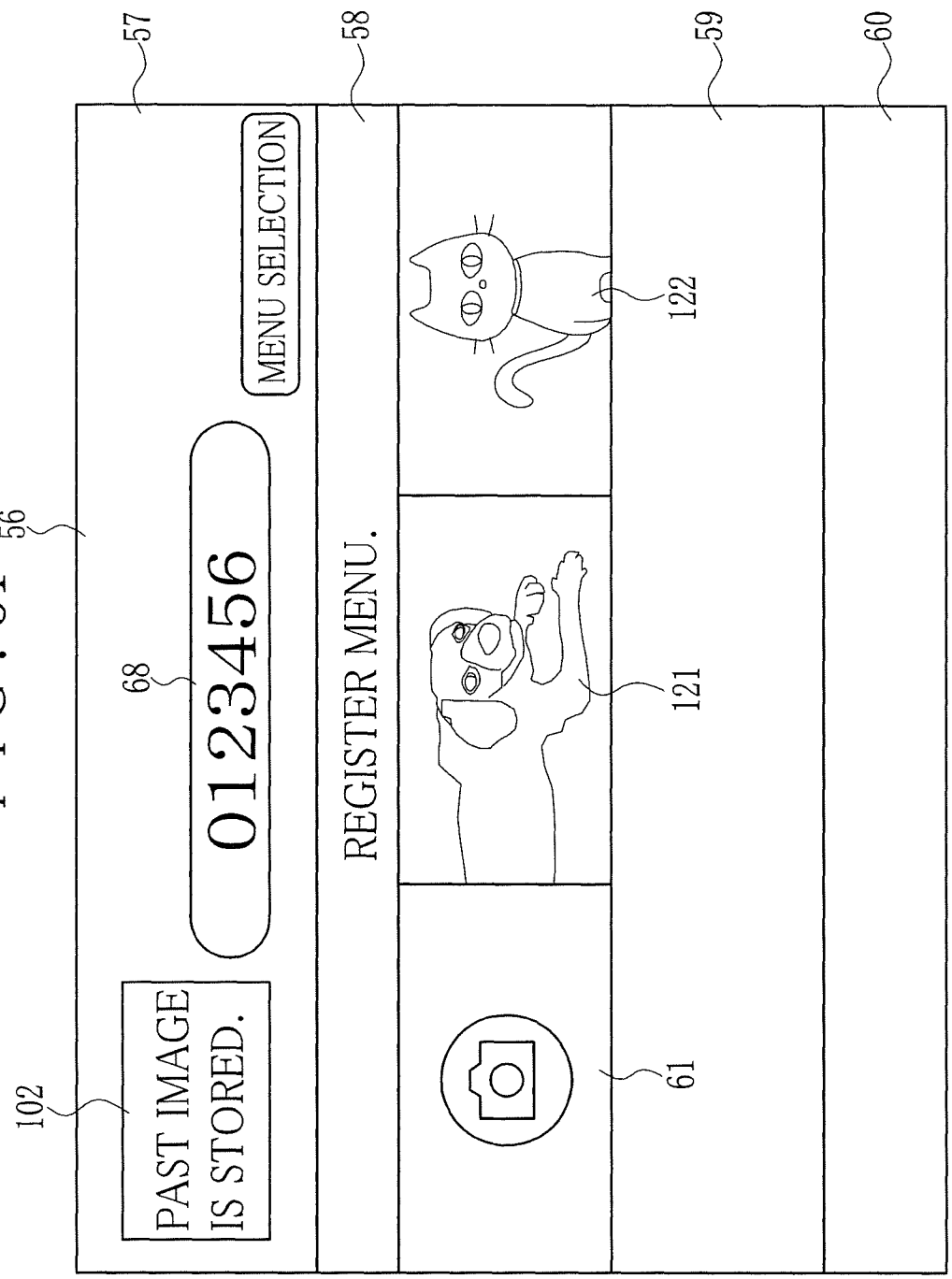

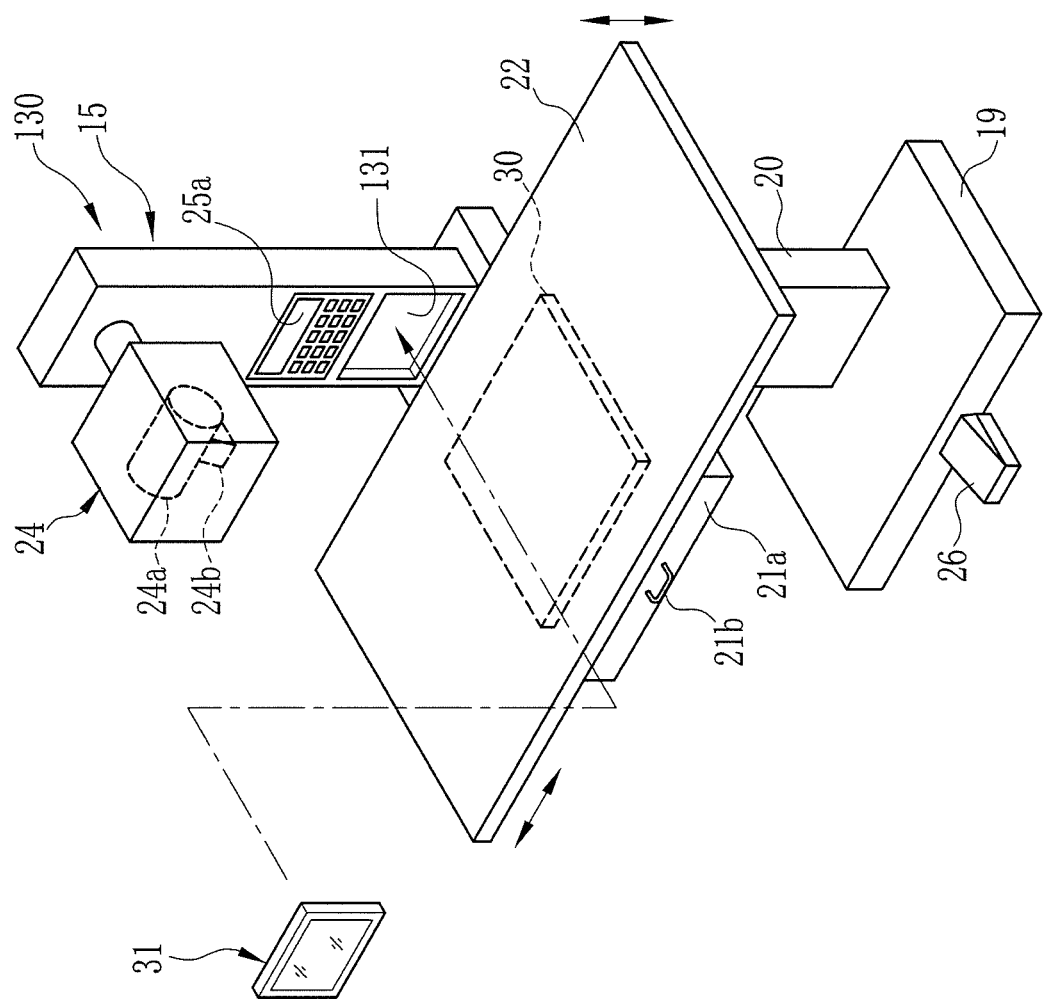

CONSOLE DEVICE OF PORTABLE TYPE, CONTROL METHOD AND RADIOGRAPHIC IMAGING SYSTEM

CROSS-REFERENCE TO RELATED APPLICATION

This application claims priority under 35 USC 119 from Japanese Patent Application No. 2014-187305, filed 16 Sep. 2014, the disclosure of which is incorporated by reference herein.

BACKGROUND OF THE INVENTION

1. Field of the Invention

The present invention relates to a console device of a portable type, a control method and a radiographic imaging system. More particularly, the present invention relates to a console device of a portable type in which visual recognition of an optical image for identification is improved, and a control method and a radiographic imaging system.

2. Description Related to the Prior Art

In the field of medicine, image diagnosis is performed by acquiring medical images of a patient. To this end, a radiographic imaging system for use with radiation such as X-rays is well-known as a system for acquiring medical images. The radiographic imaging system includes a radiation generator and a radiographic imaging apparatus. The radiation generator generates radiation. The radiographic imaging apparatus forms a radiation image of a body of a patient by detecting the radiation transmitted through the body. The radiation generator includes a radiation source, source driver and radiation switch. The radiation source applies the radiation to the body. The source driver drives and controls the radiation source. The radiation switch is operable to send an input to the source driver for starting the radiation source. The radiographic imaging apparatus includes a radiographic imaging device and a console device, which acquires (or reads) radiation images recorded by the radiographic imaging device and performs display processing for a display to display the radiation image.

There is a type of radiographic imaging device in which a radiation film or an imaging plate (IP) coated with photostimulable phosphor is used for recording a radiation image. The radiation image on the radiation film or the like is read by a scanner for the radiation film or an IP reading apparatus, and converted into image data. The console device acquires the converted image data, and displays an image of the image data. Also, a known type of radiographic imaging device is a radiation image detector, which converts radiation into an electric signal to record a radiation image. The radiation image detector includes a sensor panel called a flat panel detector (FPD), which converts the radiation transmitted through a body of the patient into an electric signal, to detect the radiation image. As the radiation image detector can transmit the radiation image to the console device immediately for the console device to display the image. There is an advantage of visually checking the present image immediately after imaging, in comparison with the conventional type of the radiographic imaging device for use with the radiation film or imaging plate.

A widely available form of the console device of the desktop type includes a display panel and a console main unit. The display panel is a display unit for displaying a user page or browse page for image browsing. The console main unit is based on a personal computer, workstation or other electronic terminal equipment, and acquires a radiation image created by the radiographic imaging device. Also, the console main unit is a display controller or display processor for outputting the user page and for driving the display panel to display the radiation image and the user page together.

The user page is displayed on the display panel for image browsing. A first user menu structure or radiographic imaging menu structure is caused to appear in the user page for manual inputs for acquiring radiation images. Examples of items in the first user menu structure include body parts and imaging directions expressed by letters, icons or the like for specifics of radiation images. In one event of the image browsing, a plurality of the first user menu structure are displayable in the user page in view of plural radiation images according to various body parts or various imaging directions.

The console main unit upon acquiring the radiation image from the radiographic imaging device displays the radiation image in the user page in association with the first user menu structure. The first user menu structure is set in a visually distinct form in a state after the imaging. Assuming that a radiation image is selected in the user page, the console main unit changes over the user page to a view page or image page (viewer screen), and displays the radiation image in an enlarged manner. A doctor or operator changes over the console device between the user page and the view page according to his or her purpose, and utilizes the console device for the image browsing or as an aid for explaining the radiation image to the patient.

JP-A 2009-089723 discloses the radiographic imaging apparatus having a portable console device, which is based on a portable terminal device such as a smart phone or tablet terminal device. The portable console device has a touchscreen display unit for displaying an image and receiving inputs in response to touch. The touchscreen display unit displays the user page in the same manner as the console device of the desktop type. The portable console device has a smaller size and smaller weight than the desktop type, and is operable in a manually held state in a hand of an operator. The portable console device is useful in various fields of health care in which an operator must work in an erect posture, for example, in a veterinary clinic, or for emergency medicine in which rapidity is essential.

In the image browsing, direct questioning (identity interrogation) to a patient is carried out before starting imaging of a radiation image. In the veterinary clinic, an animal owner of an animal (animal body) is checked by interrogation for the identification, as the direct questioning to the animal is impossible. In general, identifying the animal in connection with the animal owner is in a place outside the examination room, because of preventing unwanted exposure of radiation to the animal owner. Thus, a problem arises in that the animal owner cannot check his or her animal directly at the same time as radiographic imaging. The animal owner may feel uncertainty in the image diagnosis, as he or she is not sure that the animal on which a veterinarian explains is identical with the animal of the animal owner.

In the emergency medicine, it is likely that the direct questioning of a patient cannot be performed before the image browsing according to impairment of consciousness of the patient. For such a situation, for example, a radiation image of the patient is formed at first according to a body ID assigned to the patient of the impaired consciousness. Then the direct questioning is performed after recovery of his or her consciousness, to input patient information in combination with the body ID by use of the user page. However, errors may occur in identification. For example, a plurality of patients without the direct questioning may be present at the same time. Image browsing for each of the patients may be required one after another sequentially. Possibility of errors is higher in combining the patient IDs in the user page with the patients to be observed actually in the image browsing. It is necessary for a doctor or operator in the emergency medicine to verify a patient of the patient ID with a patient body to be observed actually.

It is conceivable to display an optical image (identification image) of an animal or patient in the user page to solve such a problem in the veterinary clinic or the emergency medicine, the optical image being a portrait image of a face with which he or she can be identified properly. It is usual in the veterinary clinic to perform the image browsing while a progress of the animal is recorded with an optical image. A user menu (second user menu structure) is preferably provided in the user page for acquiring the optical image. The veterinary clinic should be always ready for acquiring an optical image. This function will makes it possible to photograph a face of the patient or the animal and display the optical image in the user page. It is conceivable to compare the optical image with the patient or the animal always as desired by the doctor or veterinarian in relation to a current or past radiation image for the purpose of explaining the image browsing or radiation image on the basis of the user page.

However, the size of a touchscreen display unit of the portable console device useful in the veterinary clinic or for the emergency medicine is smaller than the display panel of the console device of the desktop type. An optical image (identification image) must be displayed in the portable console device for the purpose of displaying the user page containing the optical image of a patient or the animal and a second user menu structure, in addition to the first user menu structure and a radiation image. This makes it difficult to check the identity properly.

JP-A 2009-089723 does not discloses a technique of improving visual recognition of an optical image in the portable console device for checking identity.

SUMMARY OF THE INVENTION

In view of the foregoing problems, an object of the present invention is to provide a console device of a portable type in which visual recognition of an optical image for checking identity is improved, and a control method and a radiographic imaging system.

In order to achieve the above and other objects and advantages of this invention, a console device of a portable type for acquiring a radiation image of a body created by a radiographic imaging device is provided. A display controller performs display processing to display the radiation image in a user page on a display unit. The display controller performs display processing to display at least one optical image of the body in the user page on the display unit in a larger size than the radiation image.

Preferably, the display unit includes a touchscreen display unit having a longer side equal to or less than 260 mm and a shorter side equal to or less than 180 mm, in a form of a tablet terminal device.

Preferably, the display controller further causes the user page to display a first user menu structure for acquiring the radiation image, and second user menu structure for acquiring the optical image of the body in a list form.

Preferably, alphanumeric information is displayed in at least one portion of the first or second user menu structure, and has a height equal to or more than 5 mm and a width equal to or more than 5 mm.

Preferably, the display controller arranges and displays the first user menu structure adjacently with the radiation image in a display area of a size equal to the optical image.

Preferably, the display controller deletes a margin portion disposed around the body in the radiation image, to display a modified radiation image formed by deleting the margin portion.

Preferably, the body is an animal body, and the radiation image is for veterinary use.

Preferably, furthermore, an ID input unit is adapted to manually inputting a body ID for recognition of the body.

Preferably, the ID input unit is constituted by an input area within the user page, and the body ID is displayed in the user page.

Preferably, furthermore, an optical image acquisition unit actuates an optical camera unit in the tablet terminal device assuming that image acquisition is instructed in the second user menu structure, and acquires the optical image from the optical camera unit.

Preferably, the optical image is stored in an optical image storage medium in association with the body ID, and the optical image acquisition unit acquires the optical image associated with the body ID input by the ID input unit from the optical image storage medium.

Preferably, the display controller displays the optical image from the optical image storage medium in the user page. Assuming that a new optical image is acquired from the optical camera unit, the display controller updates the user page to display the new optical image in place of the optical image.

Preferably, the display controller displays the radiation image in a reduced size in the user page. Assuming that the radiation image is selected in the user page, the display controller changes over the display unit from the user page to a view page, and causes the view page to display the radiation image in an enlarged size.

Preferably, assuming that the display unit is changed over from the view page to the user page, the display controller causes the user page to display the radiation image displayed in the view page.

Preferably, the display controller outputs the user page in a scrollable manner, and in case the user page with the optical image is scrolled, performs display control to display the optical image in the user page even after scrolling.

Preferably, in case plural optical images are acquired, at least one first optical image among the optical images is displayed in the user page.

Preferably, the display controller displays information of existence of an undisplayed optical image among the plural optical images in an overlapped manner with the first optical image.

Preferably, the radiation image is stored in a radiation image storage medium in association with the body ID. Furthermore, a radiation image searcher searches a past radiation image from the radiation image storage medium according to the body ID input by the ID input unit. Assuming that the past radiation image is found to exist, then the display controller displays information of existence of the past radiation image in the user page.

Also, a control method for a portable information terminal device for acquiring a radiation image of a body created by a radiographic imaging device is provided, and includes a step of performing display processing to display the radiation image in a user page on a display unit. Display processing is performed to display at least one optical image of the body in the user page on the display unit in a larger size than the radiation image.

Also, a radiographic imaging system includes a radiographic imaging device for creating a radiation image of a body. A console device of a portable type acquires the radiation image. A console holder holds the console device. The console device includes a display controller for performing display processing to display the radiation image in a user page on a display unit. The display controller performs display processing to display at least one optical image of the body in the user page on the display unit in a larger size than the radiation image.

Consequently, visual recognition of an optical image for checking identity can be improved, because the optical image is displayed in a larger size than a radiation image.

BRIEF DESCRIPTION OF THE DRAWINGS

The above objects and advantages of the present invention will become more apparent from the following detailed description when read in connection with the accompanying drawings, in which:

FIG. 28 is a plan illustrating a user page of a third preferred embodiment;

FIG. 29 is an explanatory view illustrating an image database of a fourth preferred embodiment;

FIG. 30 is an explanatory view illustrating an image database of a fifth preferred embodiment;

FIG. 31 is a plan illustrating a user page of the fifth preferred embodiment;

FIG. 32 is a perspective view illustrating a radiographic imaging system of a sixth preferred embodiment.

DETAILED DESCRIPTION OF THE PREFERRED EMBODIMENT(S) OF THE PRESENT INVENTION

First Embodiment

Figure 1:
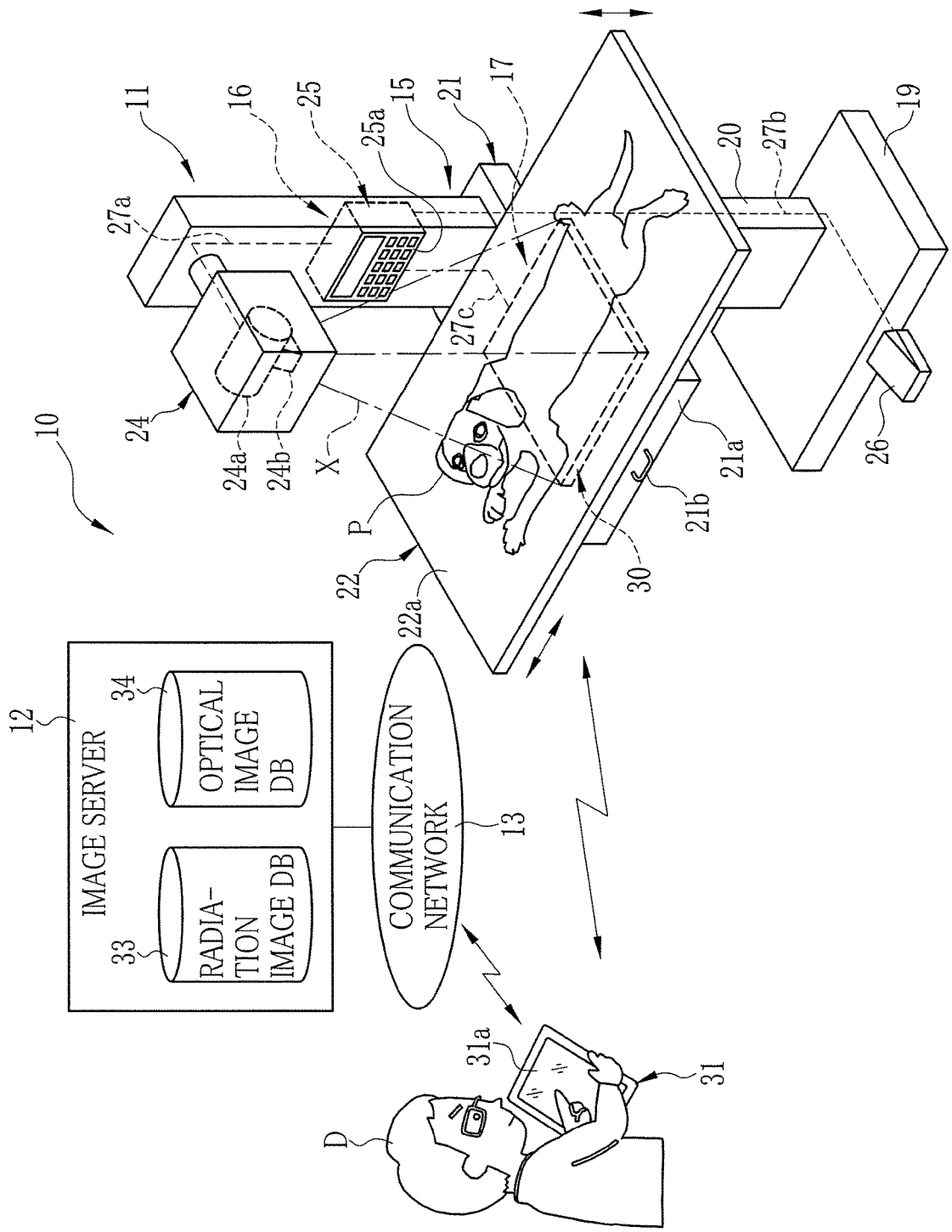
FIG. 1 is a perspective view illustrating a radiographic imaging system for veterinary use.

In FIG. 1, a radiography system architecture 10 or X-ray system architecture for veterinary use is illustrated, and used for imaging of an animal body P of an animal, for example, a dog, cat, and various pets and small animals. The radiography system architecture 10 includes a radiographic imaging system 11 or radiographic imaging apparatus for veterinary use, an image server 12 and a communication network 13. The radiographic imaging system 11 forms a radiation image of the animal body P. The image server 12 manages radiation images of the animal body P. The communication network 13 interconnects the radiographic imaging system 11 and the image server 12 in a communicable manner. An example of the communication network 13 is a local area network (LAN) installed in a veterinary clinic.

In general, most of the veterinary clinics only have small facilities. Very few veterinary clinics have an electronic medical chart system for the reason of small merit. In the present embodiment, the radiography system architecture 10 is described in a condition of an ordinary type of veterinary clinic in which medical charts of paper documents are used for recording and managing diagnostic information of an animal body P without introducing an electronic medical chart system.

The radiographic imaging system 11 is installed in an examination room in the veterinary clinic. The radiographic imaging system 11 includes a stand device 15, a radiation generator 16 or X-ray generator, and a radiographic imaging device 17 or X-ray imaging device. A patient table 22 of the stand device 15 supports an animal body P of an animal to be imaged. The radiation generator 16 emits radiation. The radiographic imaging device 17 forms a radiation image by receiving the radiation transmitted through the animal body P. The radiation generator 16 and the radiographic imaging device 17 are partially incorporated in the stand device 15. A portable console device 31 for veterinary use in the radiographic imaging system 11 is operated by a veterinarian D or operator, and can be carried and moved with portability in a site of the veterinary clinic.

The stand device 15 includes a base portion 19, a stand 20 (support post), a lift mechanism 21 and the patient table 22. The base portion 19 is placed on a floor of an examination room, and supports the entirety of the stand device 15 as a pedestal. The stand 20 is fixed on the base portion 19 to extend vertically as a pillar, to support the patient table 22.

The lift mechanism 21 is a mechanism for supporting the patient table 22, and disposed on the stand 20 in a manner movable up and down vertically. A radiation image detector 30 or electronic cassette is included in the radiographic imaging device 17. A detector holder 21a is disposed in the lift mechanism 21 for containing the radiation image detector 30. A grip handle 21b is formed on a front surface of the detector holder 21a, and used for pulling out the detector holder 21a from a lower side of the patient table 22. An inner space of the detector holder 21a contains the radiation image detector 30. Returning the detector holder 21a with the radiation image detector 30 to the lower side of the patient table 22 positions the radiation image detector 30 under the patient table 22.

The patient table 22 is used for placement of the animal body P. An upper surface 22a of the patient table 22 is kept horizontal by supporting the patient table 22 with the lift mechanism 21. The patient table 22 is in a shape of a rectangular quadrilateral extending in a horizontal direction. The lift mechanism 21 keeps the patient table 22 movable horizontally in its longitudinal direction. Moving the patient table 22 with the animal body P causes a body part of the animal body P to face the radiation image detector 30.

The radiation generator 16 includes a radiation source 24 or X-ray source, a source driver 25 and a radiation switch 26. The radiation source 24 applies radiation or X-rays to the animal body P on the patient table 22. The source driver 25 controls the radiation source 24. Signal cables 27a and 27b are extended into the base portion 19 and the stand 20, and used to connect the radiation source 24 and the radiation switch 26 to the source driver 25.

The radiation source 24 is supported on an upper portion of the stand 20 and opposed to the patient table 22. The radiation source 24 includes an X-ray tube 24a and a collimator 24b. The X-ray tube 24a emits X-rays X as radiation. The collimator 24b limits a radiation field of radiation from the X-ray tube 24a.

The source driver 25 generates a control signal according to an imaging condition and controls the radiation source 24 by use of the control signal. Values in the imaging condition are a tube voltage, tube current, irradiation time and the like. The tube voltage determines energy spectrum of the radiation. The tube current determines dose of the radiation per unit time. The irradiation time is time of continuing the irradiation of the radiation. The control signal is transmitted by the signal cable 27a to the radiation source 24. A control panel 25a is disposed in the source driver 25 for setting the imaging condition. The control panel 25a includes plural buttons and a display panel. The buttons are used for setting the imaging condition. The display panel displays the imaging condition. The source driver 25 is disposed in the stand 20. The control panel 25a appears externally through the front side of the stand 20. The source driver 25 is disposed between the patient table 22 and the radiation source 24 for the veterinarian to touch the control panel 25a while he or she keeps the animal body P placed on the patient table 22.

The radiation switch 26 is a foot pedal type of switch. A veterinarian D or operator can depress the radiation switch 26 with his or her foot while he or she holds the animal body P on the patient table 22 with both hands. The radiation switch 26 generates a start signal for starting the radiation source 24 to emit radiation. The start signal of the radiation switch 26 is input to the source driver 25 through the signal cable 27b.

The source driver 25 controls the radiation source 24 according to a signal from the radiation switch 26. In case a start signal is received from the radiation switch 26, the source driver 25 starts supplying the radiation source 24 with power, to drive the radiation source 24 to emit radiation. At the same time as the start, the source driver 25 starts a timer to measure irradiation time or elapsed time. In case the elapsed time becomes as long as a predetermined duration according to the imaging condition, the irradiation of the radiation is stopped. The irradiation time of the radiation is changeable according to an irradiation condition. In the source driver 25, longest tolerable time for safety of the irradiation is predetermined. The irradiation time according to the irradiation condition is set within a range of the longest tolerable time.

Figure 3:
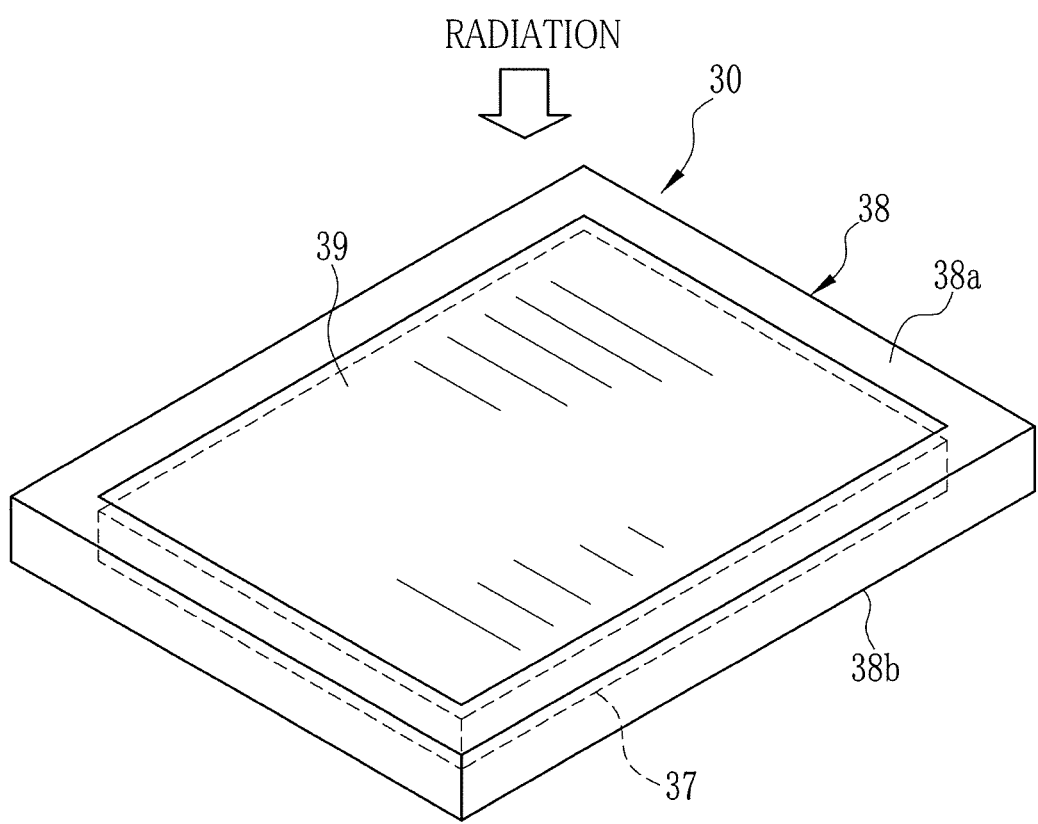
FIG. 3 is a perspective view illustrating a radiographic imaging device.

The radiographic imaging device 17 includes the radiation image detector 30 and the portable console device 31 for veterinary use. The radiation image detector 30 detects a radiation image. The portable console device 31 is a user terminal device in connection with the radiation image detector 30, for acquiring and displaying the radiation image. A portable housing 38 in FIG. 3 is included in the radiation image detector 30, and has a flat shape with a small thickness in a quadrilateral shape. The housing 38 is in a form according to the International Standards ISO 4090: 2001 for a film cassette of IP cassette (imaging plate cassette). The radiation image detector 30 is generally referred to as an electronic cassette. A sensor panel 37 in FIG. 3 is contained in the housing 38, and converts radiation transmitted through the animal body P into an electric signal, to detect the radiation image.

A signal cable 27c in the stand device 15 connects the radiation image detector 30 to the source driver 25. The radiation image detector 30 receives the imaging condition and sync signals from the source driver 25 through the signal cable 27c. The imaging condition is utilized for setting a condition of the signal processing in the sensor panel 37 at the time of detecting a radiation image. The sync signals include a start flag signal for notifying a start of irradiation of the radiation source 24, and an end flag signal for notifying an end of the irradiation. The sensor panel 37 starts detecting of the radiation image in response to the start flag signal, and ends the detection of the radiation image in response to the end flag signal. The radiation image detector 30 transmits the detected radiation image to the portable console device 31.

The portable console device 31 is constituted by a tablet terminal device. A touchscreen display unit 31a or touchscreen interface (touch panel) is disposed in a front wall of the portable console device 31 for display and touch operation. The touchscreen display unit 31a corresponds to a display unit of the invention. The portable console device 31 is connected to the radiation image detector 30 and the communication network 13 in a communicable manner by radio communication. The portable console device 31 has a small size, small weight and high portability remarkably in comparison with a desktop type of console device being available widely. It is possible for a veterinarian or operator to carry the portable console device 31 in a veterinary clinic and operate the portable console device 31 easily with his or her hands.

Figure 2:
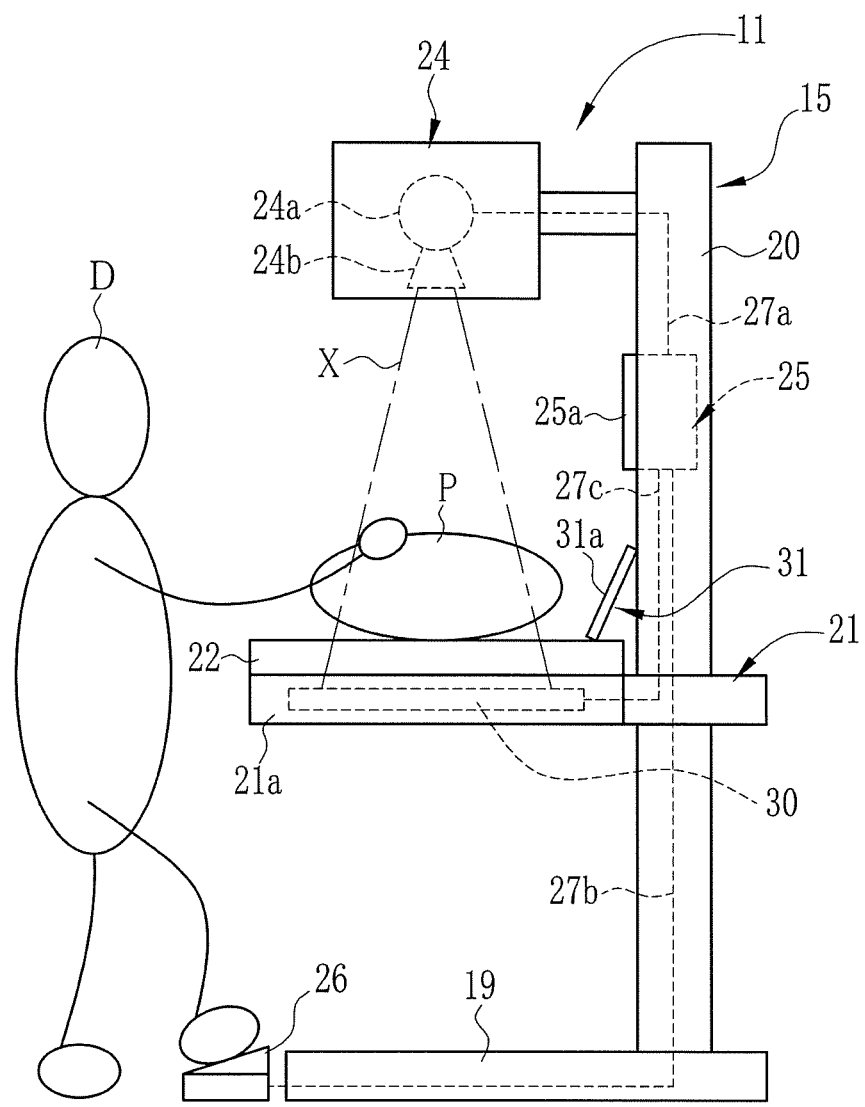
FIG. 2 is a side elevation illustrating the radiographic imaging system.

In FIG. 2, the portable console device 31 may be oriented in an erect posture at a distance from the veterinarian D or operator, typically in case he or she keeps the animal body P placed on the patient table 22 for radiographic imaging. In the drawing, the portable console device 31 is leaned on the patient table 22 for positioning. However, the portable console device 31 can be positioned on a support plate or the like near to the stand device 15, for example, in case the animal body P is very likely to move abruptly, in case the portable console device 31 may be made dirty by body liquid or the like from the animal.

The portable console device 31 is operable in two operation modes including an image browsing mode and an image viewing mode. In the image browsing mode, images are read out and browsed. In the image viewing mode, radiation images of past image browsing are viewed. The portable console device 31 is set in a selected one of the image browsing mode and image viewing mode, and used for the image browsing or viewing radiation images.

The portable console device 31 set in the image browsing mode receives an input of a body ID for identifying the animal body P and receives registration of a first user menu structure for acquiring a radiation image. The body ID and the first user menu structure are displayed on the touchscreen display unit 31a. As information with relevancy to the imaging of the radiation image in registering the first user menu structure, animal type information and imaging information is set in relation to the animal body P and the imaging. The animal type information includes information of animal types such as a dog, cat, bird, reptile and the like, and information of size of the animal body. The imaging information includes information of body parts such as a thorax, abdomen and head, and information of imaging directions such as front, lateral and diagonal directions. The animal type information and imaging information is transmitted to the radiation image detector 30, and utilized for condition setting of the signal processing described above. The radiation image detector 30 after the condition setting transmits a ready signal to the portable console device 31 to inform a ready state after preparation. Thus, a veterinarian D or operator at the portable console device 31 can find the ready state of the radiation image detector 30.

The portable console device 31 in the image browsing mode receives a radiation image from the radiation image detector 30, and drives the touchscreen display unit 31a to display the radiation image. After the image browsing, the radiation image is transmitted from the portable console device 31 to the image server 12.

The portable console device 31 in the image browsing mode is also used for photographing an optical image of the animal body P. The touchscreen display unit 31a displays a second user menu structure for acquiring the optical image. Also, the formed optical image of the animal body P is displayed on the touchscreen display unit 31a. For example, the optical image of the animal body P is photographed in the examination room shortly before the start of the image browsing. After obtaining the optical image, the portable console device 31 is carried by the veterinarian D or operator to the animal owner waiting outside the examination room, to show him or her the optical image of the animal body P on the portable console device 31. This is effective in preventing misidentification of the animal of the animal body P even in presence of the other animals. The animal body P can be identified as reliably as for a human patient in the human medicine.

Also, the veterinarian D can compare and check the optical image on the portable console device 31 with the animal body P before radiographic imaging. Errors in identifying the animal body P can be prevented reliably in comparison with the use of only the body ID. Also, the optical image of the animal body P remains displayed on the same display even while the veterinarian D shows the radiation image on the portable console device 31 to the animal owner and explains the progress. Thus, the animal owner can confirm the identity of the animal body P of his or her animal in relation to the radiation image. Furthermore, the veterinarian D can check and review the progress of the animal body P, because the optical image of the animal body P is displayed even while radiation images of the past image browsing are viewed in the image viewing mode.

The optical image of the animal body P can have such a form that a portion of the animal body P with visual distinction appears in an image area of the optical image. For example, a face image of the animal body P is photographed assuming that the animal body P is distinguished by its face. A skin hair image or surface pattern image of the animal body P is photographed assuming that the animal body P is distinguished by its skin hair or surface pattern. The optical image of the animal body P is transmitted to the image server 12 together with the radiation image.

The portable console device 31 set in the image viewing mode sends a request of image distribution to the image server 12. Then the portable console device 31 receives past radiation images and past optical images from the image server 12 upon transmission of the distribution request. The radiation images and optical images being received are ready to be displayed on the touchscreen display unit 31a.

The image server 12 is a server for managing the radiation image and optical image from the portable console device 31. The image server 12 is installed in the veterinary clinic in the embodiment, but may be disposed in a data center or information center in a site separate from the veterinary clinic. The image server 12 includes a radiation image database 33 (DB) as a radiation image storage medium, and an optical image database 34 (DB) as an optical image storage medium. The radiation image database 33 stores radiation images. The optical image database stores optical images. The image server 12 writes the radiation image and optical image to respectively the image databases 33 and 34 upon receiving those from the portable console device 31. Also, the image server 12 performs search in the image databases 33 and 34 in response to a request of distribution from the portable console device 31 in the image viewing mode, and transmits the searched radiation image and optical image to the portable console device 31.

In FIG. 3, the radiation image detector 30 includes the sensor panel 37 and the housing 38 for containing the sensor panel 37. An imaging surface 38a is a front surface of the housing 38 and receives radiation. A back surface 38b is opposite to the imaging surface 38a in the housing 38. The imaging surface 38a and the back surface 38b are in a shape of a rectangular quadrilateral. A radio-transparent plate 39 is included in the housing 38 to constitute the imaging surface 38a, and transmits radiation or X-rays.

The sensor panel 37 is an indirect conversion type having a scintillator and a photoconductor (not shown). The scintillator converts radiation into visible light. The photoconductor converts the visible light into an electric signal. An example of the photoconductor is a TFT active matrix board, and has an imaging area having plural pixels arranged in a two-dimensional manner for storing charge according to dose of incident radiation. Each pixel is constituted by a photo diode and a TFT. An example of the scintillator is phosphor such as cesium iodide, and is opposed to the entire surface of the imaging area.

The housing 38 contains various elements in addition to the sensor panel 37, inclusive of a control circuit board, communication control unit, battery (not shown) and the like. The control circuit board includes a gate driver, readout circuit, A/D converter, memory and the like. The gate driver drives photoconductors in the sensor panel 37. The readout circuit reads out an image signal from the photoconductors. The A/D converter converts the read image signal into digital data of a radiation image. The memory stores the radiation image. The communication control unit has a radio communication interface for radio communication with the portable console device 31. The battery supplies the sensor panel 37 and the other elements with power. The radiation image detector 30 is a wireless type having the radio communication circuit, and can be easily handled because of unnecessity of a power cable by use of the battery.

Figure 4:
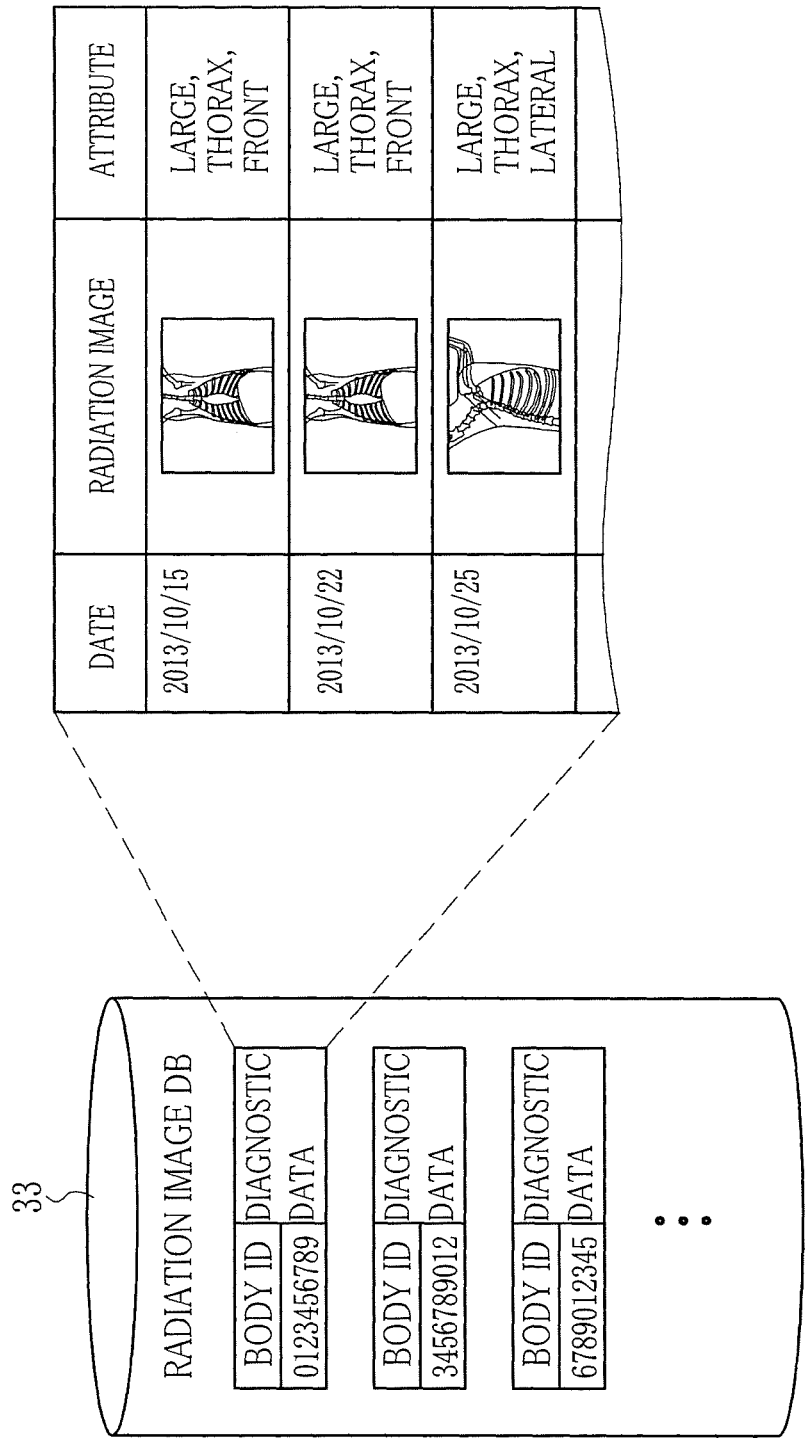
FIG. 4 is an explanatory view illustrating a radiation image database.

In FIG. 4, the radiation image database 33 stores plural diagnostic data including at least one radiation image formed by the radiographic imaging system 11. A body ID for the animal body P is assigned to the radiation image, and can be used for searching the radiation image. In the diagnostic imaging, plural radiation images may be formed by imaging the body for plural body parts or in plural imaging direction in one event of the imaging. A case ID is assigned to the set of the plural radiation images of the one imaging event, to manage the radiation images together. In the diagnostic data, the radiation images are managed per the date and time of the diagnostic imaging. Also, attribute information is assigned to each of the radiation images. Data in the attribute information include animal type information and imaging information determined upon registering the first user menu structure.

Figure 5:
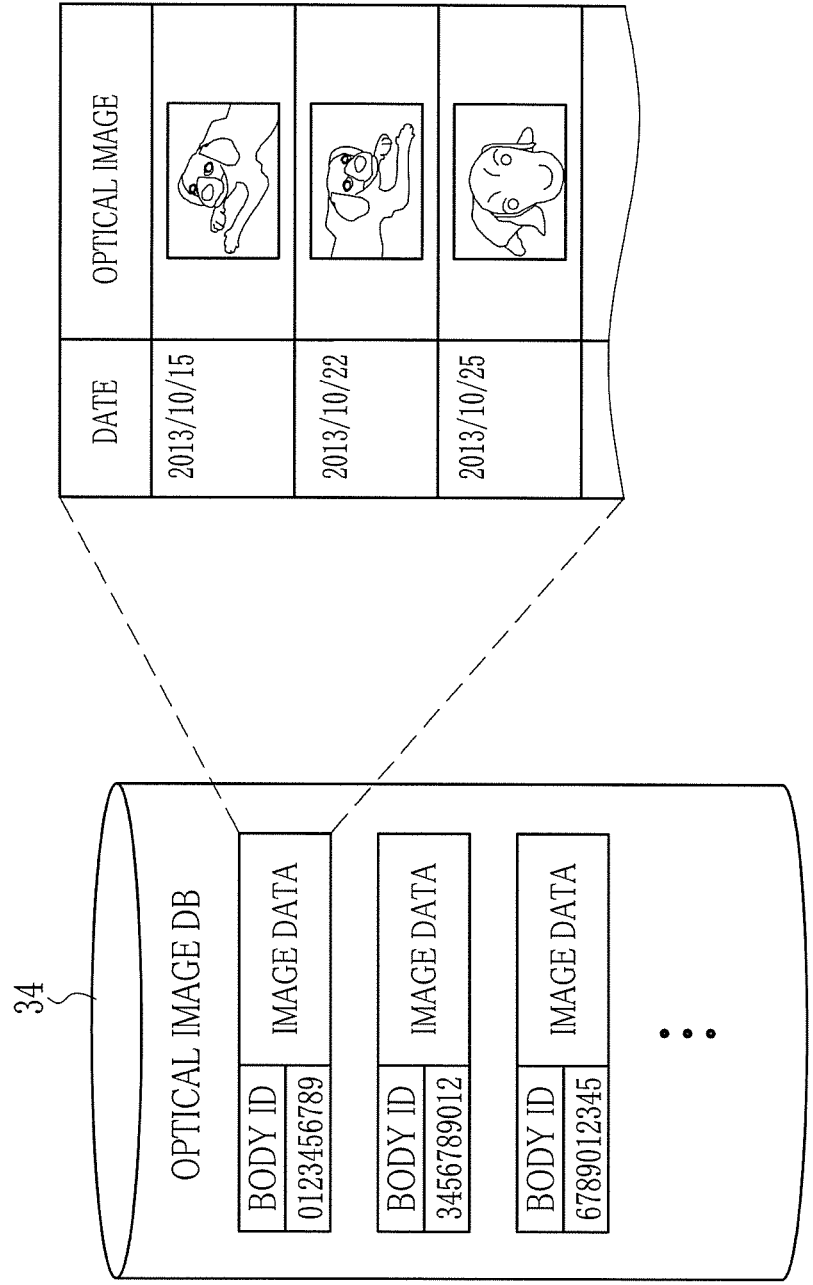
FIG. 5 is an explanatory view illustrating an optical image database.

In FIG. 5, the optical image database 34 stores body image data including optical images of the animal body P. The optical images are assigned with body IDs, with which the optical images can be searched. Assuming that it is difficult to identify the animal body P by use of the optical images, it is possible to record a plurality of optical images in one event of imaging. Also, optical images are utilized not only for identifying the animal body P but also for recording a progress note of injury, a state of skin, or the like. To this end, plural optical images may be recorded at one event of imaging. Plural optical images obtained in the imaging of one event are assigned with a single case ID and managed as optical images of one case. Also, optical images in body image data are managed for date and time of performing the diagnostic imaging.

Figure 6:
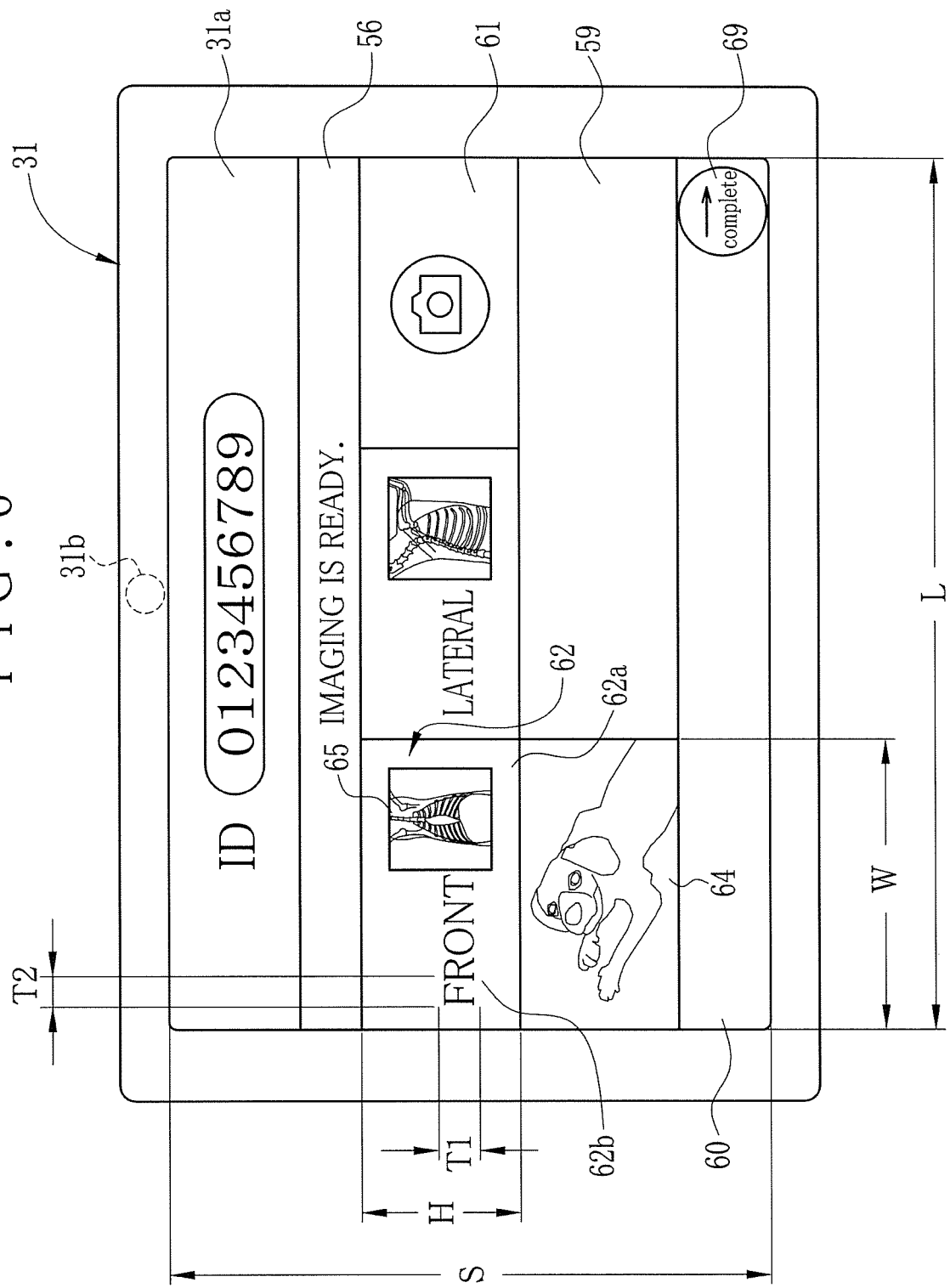
FIG. 6 is a plan illustrating a console device of a portable type.

In FIG. 6, the portable console device 31 is used in a state of horizontally extending the touchscreen display unit 31a of a quadrilateral form, or vertically extending the same. An optical camera unit 31b or optical image forming unit is disposed in a back surface of the portable console device 31 for photographing the animal body P to form an optical image. A user page 56 or browse page (input screen) is displayed on the touchscreen display unit 31a for the image browsing. The user page 56 includes a sample window area 59 or list display area, which displays a first user menu structure 62 or radiographic imaging menu structure, a second user menu structure 61 or optical imaging menu structure, an optical image 64 (identification image), and a radiation image 65 in a list form. The first user menu structure 62 includes a display area 62a and attribute information 62b or alphanumeric information. The display area 62a extends horizontally in a form of a rectangular quadrilateral. The attribute information 62b is displayed in the display area 62a and represents the animal type information and imaging information. Note that the animal type information and imaging information can be an abbreviated form of letters or indicia instead of words. The display area 62a is an active input area (active touch area) to respond to manual touch.

The tablet terminal device as a basis of the portable console device 31 is a tablet terminal device of which the touchscreen display unit 31a is in a size with a length (L) equal to or less than 260 mm and a width (S) equal to or less than 180 mm, namely in a screen size of 12 inches or less. This is for the reason of easy handling in manually operating the portable console device 31 while the animal body P is set suitably, and handlability in carrying the portable console device 31 in order to show optical images or radiation images of the animal body P to its animal owner. Note that the touchscreen display unit 31a should have a sufficiently large size for the purpose of ensuring operability of the user page 56 and recognition of radiation images. The size of the touchscreen display unit 31a preferably can be equal to or more than 7 inches.

The portable console device 31 is used not only while held manually by a hand but also while placed distantly from the veterinarian D. While the portable console device 31 is placed distantly, visual recognition of the portable console device 31 to the veterinarian D may be considerably poor assuming that a size of the attribute information 62b on the touchscreen display unit 31a is small. In the portable console device 31 of the present embodiment, each of the height T1 and width T2 of the attribute information 62b in the menu are set equal to or more than 5 mm. Should the height T1 and width T2 of the attribute information 62b be too large, an area for displaying a radiation image or optical image of the animal body P will be too small. Thus, each of the height T1 and width T2 of the attribute information 62b in the menu can be preferably set equal to or less than 20 mm.

Note that the height T1 and width T2 of the attribute information 62b are determined by an experiment of recognition. The experiment of recognition was conducted. To this end, specifically, the portable console device 31 was positioned at a point distant from a human subject with a predetermined distance. Samples of the attribute information 62b with differences in the height T1 and width T2 were displayed one after anther, to measure recognition of the human subject at each one of sizes of letters in the samples. An example of the distance between the human subject and the portable console device 31 was set from a maximum distance of the portable console device 31 from a veterinarian D, for example, 1 meter. As a result of the experiment of the recognition, recognizable sizes of the attribute information 62b were found as each of the height T1 and width T2 equal to or more than 5 mm.

As the touchscreen display unit 31a of the portable console device 31 is operated by manual touch of a finger or the like, errors in operation are likely to occur assuming that an active input area of the touchscreen display unit 31a is excessively small. In the present embodiment, a height H and width W of the display area 62a or active input area in the first user menu structure 62 are set respectively equal to or more than 13 mm.

Figure 7:
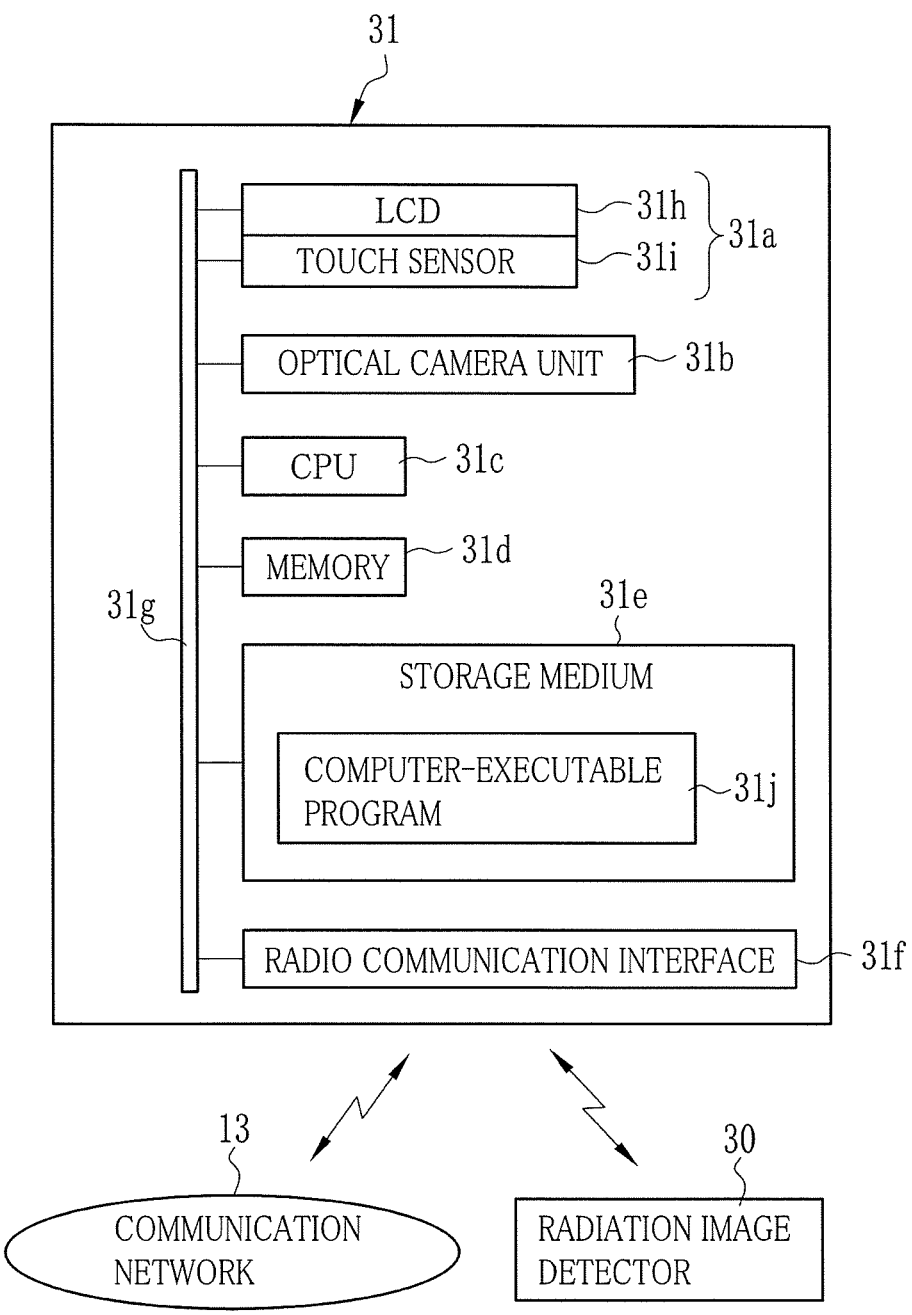
FIG. 7 is a block diagram schematically illustrating the console device.

The portable console device 31 is on the basis of a tablet terminal device having the touchscreen display unit 31a with a size equal to or less than 12 inches, and is constituted by installing a control program, such as an operating system (OS), an application program, and the like. In FIG. 7, the portable console device 31 includes the touchscreen display unit 31a, a console housing, the optical camera unit 31b, a CPU 31c, a memory 31d, a storage medium 31e or storage device, and a radio communication interface 31f. A data bus 31g interconnects the touchscreen display unit 31a, the optical camera unit 31b, the CPU 31c, the memory 31d, the storage medium 31e and the radio communication interface 31f.

The touchscreen display unit 31a includes a liquid crystal display panel 31h (LCD) and a touch sensor 31i for detecting touch on the liquid crystal display panel 31h. The portable console device 31 receives inputs of manual operation by detecting touch on the liquid crystal display panel 31h with the touch sensor 31i. The optical camera unit 31b is previously incorporated in the tablet terminal device as a basis, and includes a taking lens and an image sensor (not shown) for forming an image focused by the taking lens.

The storage medium 31e is a device for storing various data, for example, a non-volatile memory. The storage medium 31e stores the control program (not shown) described above, and a computer-executable program 31j or portable console program. The computer-executable program 31j is an application program for the tablet terminal device to function as the portable console device 31. Also, the storage medium 31e stores radiation images received from the radiation image detector 30 or the image server 12, and optical images acquired by the optical camera unit 31b.

The memory 31d is a working memory with which the CPU 31c performs tasks. The CPU 31c loads the memory 31d with the control program and the computer-executable program 31j read from the storage medium 31e, and controls various elements in the tablet terminal device by performing the tasks by running the programs. The radio communication interface 31f is an interface for wireless connection to the communication network 13 and to the radiation image detector 30.

Figure 8:
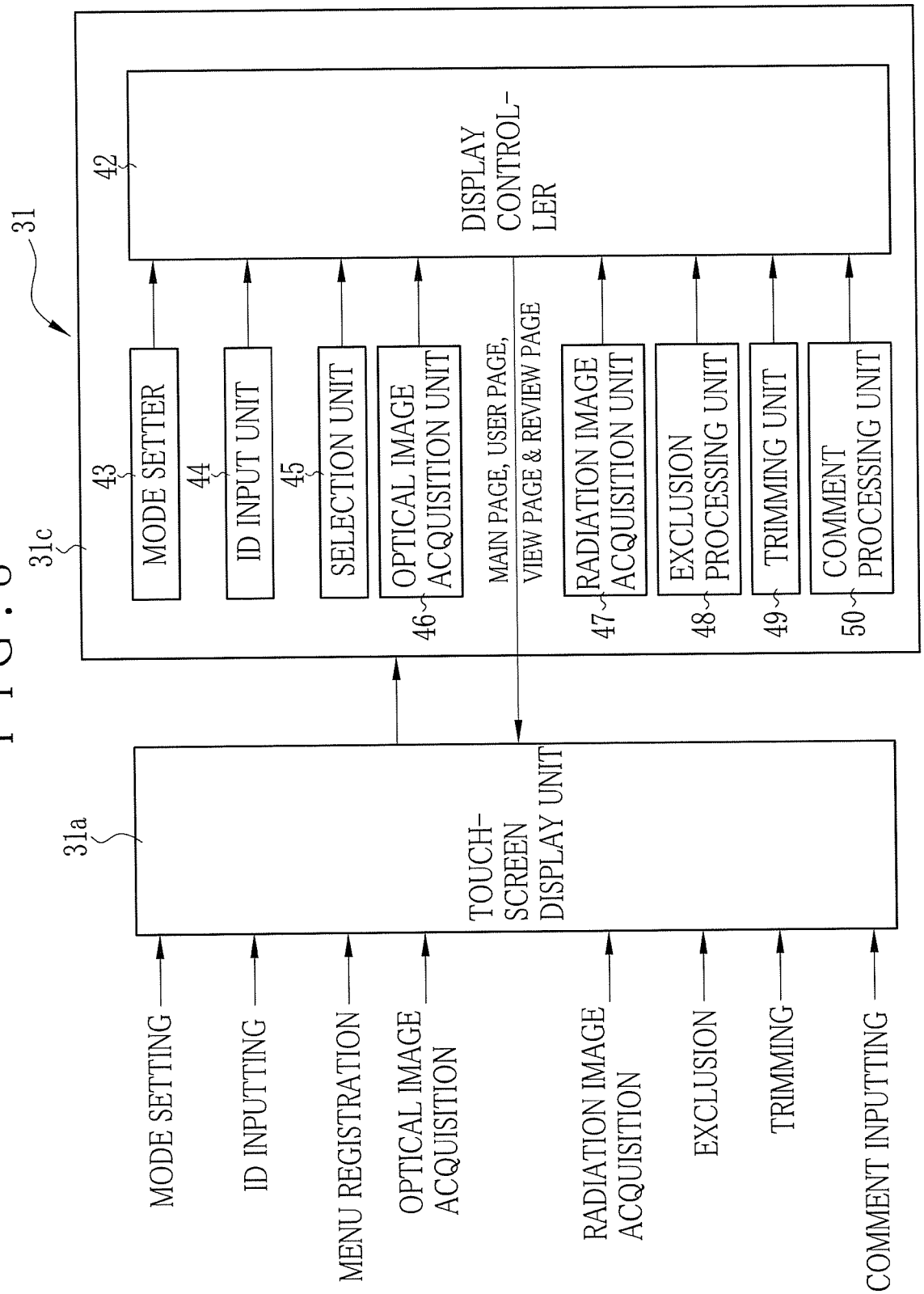
FIG. 8 is a block diagram schematically illustrating circuit devices in a CPU in the console device.

In FIG. 8, the CPU 31c is caused to have various elements upon running the computer-executable program 31j in the portable console device 31, the various elements including a display controller 42, a mode setter 43, an ID input unit 44, a selection unit 45 or menu registration unit, an optical image acquisition unit 46, a radiation image acquisition unit 47, an exclusion processing unit 48 or turn-off processing unit, a trimming unit 49 and a comment processing unit 50. The display controller 42 in response to operation of the portable console device 31 creates various pages (screen views) inclusive of a main page or mode setting page (home screen), the user page 56, a view page or image page (viewer screen), and the like, which are displayed on the touchscreen display unit 31a. The mode setter 43 sets one of an image browsing mode and image viewing mode for an operation mode in response to the mode setting detected by the touchscreen display unit 31a.

The ID input unit 44 performs processing of ID reception to receive the body ID for the animal body P in response to an input of ID detected by the touchscreen display unit 31a. The selection unit 45 performs processing of menu registration to register the first user menu structure according to an input of the menu registration detected by the touchscreen display unit 31a. The optical image acquisition unit 46 performs processing of optical image acquisition to acquire the radiographic image of the animal body P according to an input of the optical image acquisition detected by the touchscreen display unit 31a. The radiation image acquisition unit 47 performs processing of radiographic image acquisition to acquire the radiographic image according to an input of the radiographic image acquisition detected by the touchscreen display unit 31a.

The exclusion processing unit 48 responds to a command signal of image exclusion detected by the touchscreen display unit 31a, and performs image exclusion to set a formed radiation image as an excluded image without use for image browsing. The trimming unit 49 responds to a command signal of trimming detected by the touchscreen display unit 31a, and performs trimming to extract a predetermined area within the radiation image. The comment processing unit 50 responds to a command signal of comment detected by the touchscreen display unit 31a, and performs comment processing to add the comment to the radiation image.

Figure 9:
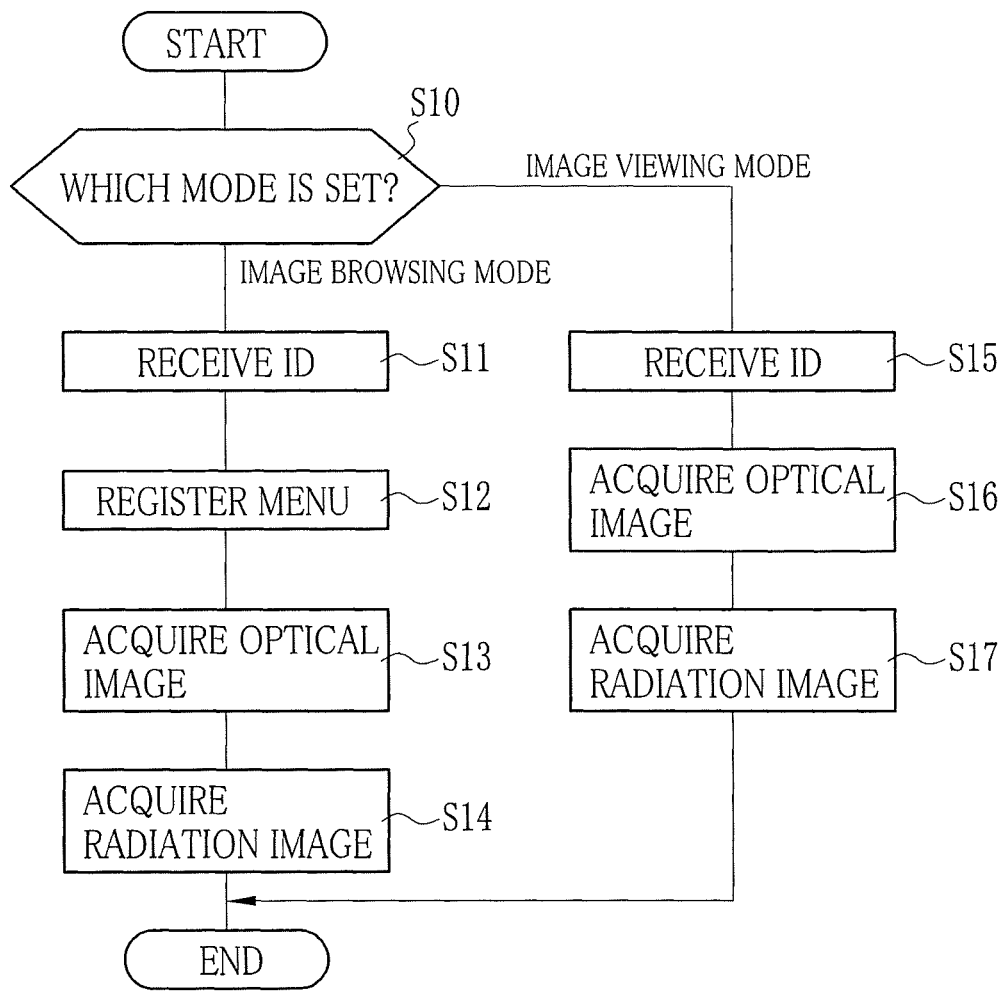
FIG. 9 is a flow chart illustrating a flow of operation in the console device.

In FIG. 9, the portable console device 31 performs a task of the mode setting (S10) for setting an operation mode. In case the image browsing mode is set in the mode setting, the ID reception (S11), the menu registration (S12), the optical image acquisition (S13) and the radiation image acquisition (S14) are performed sequentially. In the ID reception, the body ID is received. In the menu registration, a user menu structure for radiation image acquisition is registered. In the optical image acquisition, an optical image of the animal body P is acquired. In the radiation image acquisition, a radiation image of the animal body P is acquired. The display controller 42 processes the display screen according to results of the tasks, and drives the touchscreen display unit 31a to display the display screen. Note that the menu registration (S12) may be performed after the optical image acquisition (S13) according to a sequence of manual input of the veterinarian D. In case the image viewing mode is set in the mode setting, the ID reception (S15), the radiographic image acquisition (S16) and the optical image acquisition (S17) can be performed in this sequence.

Figure 10:
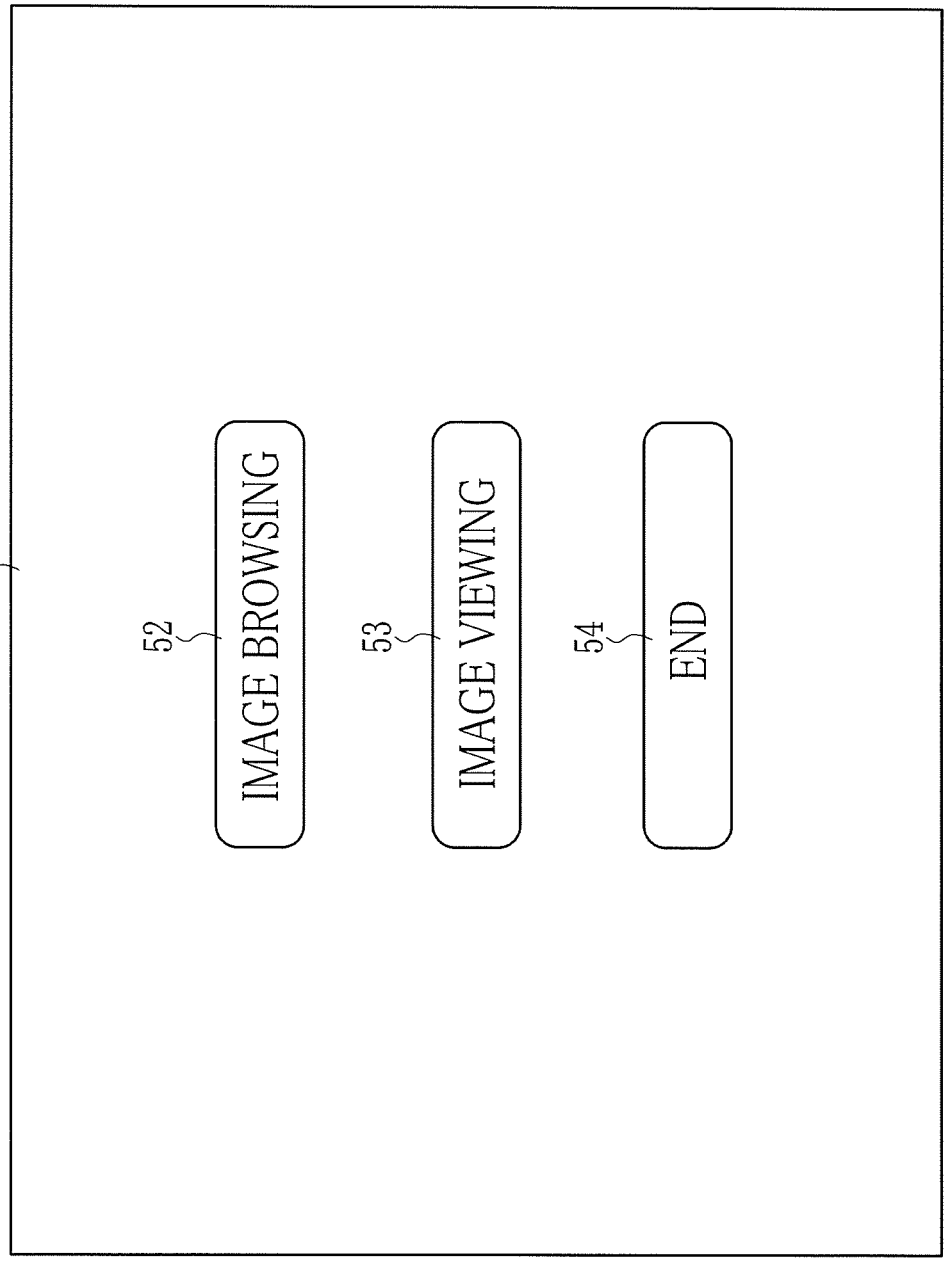
FIG. 10 is a plan illustrating a main page in the console device.

In FIG. 10, a main page 51 or mode setting screen is displayed on the touchscreen display unit 31a by the display controller 42 in a mode setting step in a form of GUI (graphical user interface) for manual operation. A veterinarian D or operator touches the touchscreen display unit 31a with fingers or the like to operate the main page 51 and other screen view. The main page 51 includes an image browsing button 52, an image viewing button 53 and an end button 54. The image browsing button 52 changes over the portable console device 31 to the image browsing mode. The image viewing button 53 changes over the portable console device 31 to the image viewing mode. The end button 54 terminates the computer-executable program 31j. The mode setter 43 sets the operation mode of the portable console device 31 according to mode setting of the main page 51.

Figure 11:
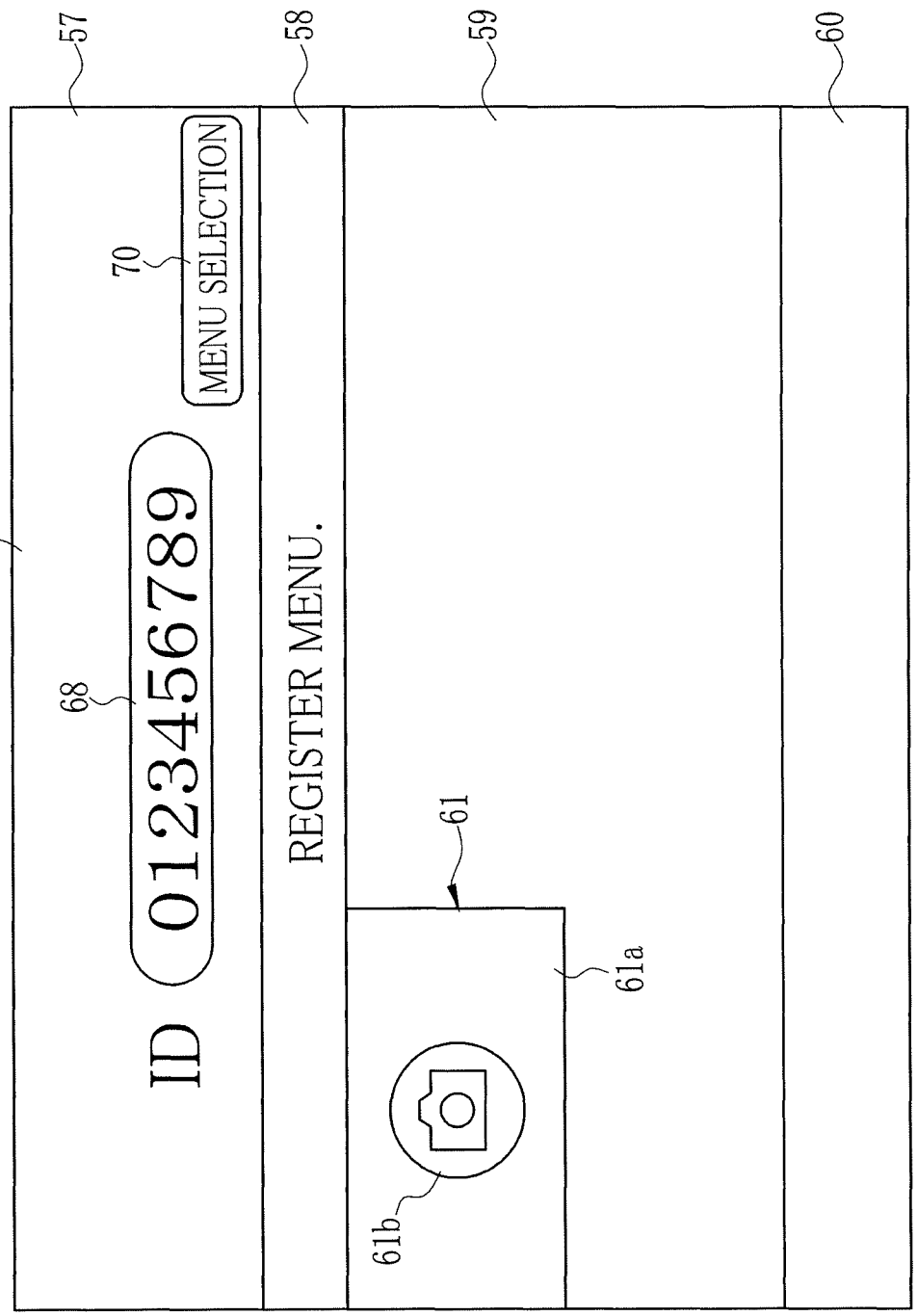
FIG. 11 is a plan illustrating a user page.

Changing over the portable console device 31 to the image browsing mode changes over the touchscreen display unit 31a from the main page 51 to the user page 56 for the image browsing as illustrated in FIG. 11. As described heretofore, the user page 56 corresponds to a browse page of the invention. The user page 56 includes an ID input area 57, a status display area 58, the sample window area 59 and an end button area 60 in a downward sequence in the drawing. The ID input area 57 extends horizontally.

The sample window area 59 displays the first user menu structure 62, a first user menu structure 63 or radiographic imaging menu structure (in FIG. 13), and the second user menu structure 61 for acquisition of an optical image of the animal body P. Also, the sample window area 59 displays the optical image (identification image) (in FIG. 15) of the animal body P acquired by use of the second user menu structure 61, and the radiation image 65 and a radiation image 66 (in FIG. 19) of the animal body P acquired by use of the first user menu structures 62 and 63. The second user menu structure 61 becomes displayed in the sample window area 59 immediately after changeover to the image browsing mode. The first user menu structures 62 and 63, the optical image 64 and the radiation images 65 and 66 are additionally displayed in the sample window area 59 in the progress of the image browsing.

Consequently, it is possible at one glance for the veterinarian D to recognize the progress of the image browsing inclusive of completed steps, in combined appearance of the second user menu structure 61, the first user menu structures 62 and 63, the optical image 64 and the radiation images 65 and 66. Also, the second user menu structure 61 and the first user menu structure 62 or 63 can be manually operated to start succeeding tasks immediately after recognizing the progress of the image browsing. Operability can be considerably increased by combining displayed forms of the images for the progress of the image browsing and the menu structures in the same user page.

An ID input field 68 is disposed in the ID input area 57 for inputting ID information. The ID input field 68 upon being touched is changed over for a state of receiving an input of the body ID. A cursor movable together with alphanumeric information of input letters is indicated in the ID input field 68. Also, a software keyboard (not shown) is displayed in a lower portion of the user page 56 for inputting the body ID, for example, in a portion overlapping on the sample window area 59. In case a body ID with alphanumeric information of letters of a predetermined number is input, the ID input field 68 is changed over from a receiving state to an indication state, and indicates the input body ID.

In a veterinary clinic having an electronic medical chart system, the radiography system architecture 10 is connected to the electronic medical chart system so that a body ID can be acquired from the electronic medical chart system. However, an ordinary type of veterinary clinic uses medical charts of paper documents for recording and managing diagnostic information of an animal body P without introducing an electronic medical chart system. Thus, the ID input field 68 is provided in the present embodiment for manually inputting body IDs for use in an ordinary veterinary clinic without having an electronic medical chart system. Note that manual operation for inputting body IDs is likely to be wrong incidentally with human operation. However, the ID input field 68 in the user page 56 displays an input body ID continuously, so that a veterinarian can be aware of his or her error upon incidental occurrence after a body ID is input. Also, an optical image according to the input body ID is displayed in the user page 56. Errors in inputting a body ID can be discovered easily, because the optical image can be used for a confirmation image for the body ID.

The status display area 58 displays a message according to a status of the sample window area 59. For example, the status display area 58 displays a message of "REGISTER MENU" (select) assuming that the first user menu structure 62 or 63 is not registered in the sample window area 59, or assuming that imaging of radiation images according to the first user menu structure 62 or 63 registered in the sample window area 59 has been completed. Also, the status display area 58 displays a message of "IMAGING IS READY" assuming that the first user menu structure 62 or 63 before imaging is displayed in the sample window area 59 and assuming that a ready signal according to the first user menu structure 62 or 63 is received from the radiation image detector 30.

In the end button area 60, an end button 69 (in FIG. 19) is displayed for indicating an end of the image browsing. Upon completion of imaging of radiation images in relation to the first user menu structures 62 and 63 displayed in the sample window area 59, the end button 69 becomes displayed in the end button area 60. Depression of the end button 69 causes the portable console device 31 to transmit radiation images of the animal body P from the radiation image detector 30 and formed optical images to the image server 12. Also, the portable console device 31 ends the image browsing mode and returns to the mode setting. The touchscreen display unit 31*a* displays the main page 51.

Figure 12:
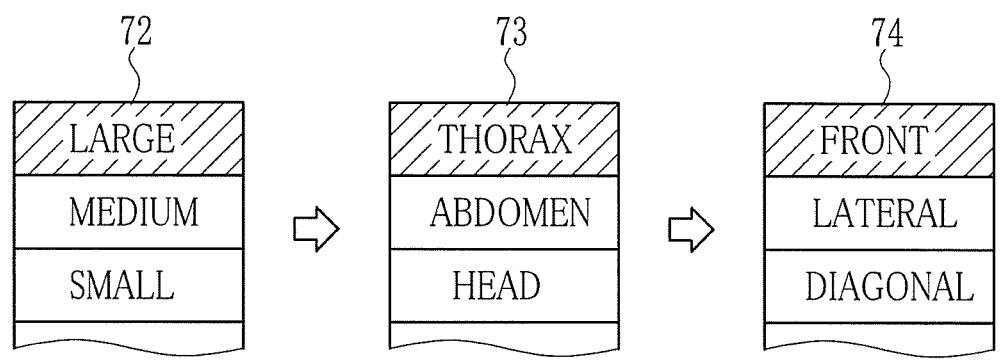
FIG. 12 is a chart illustrating a list displayed in menu registration.

A selection button 70 or menu registration button in the ID input area 57 is used for menu registration. In FIG. 12, an animal type list 72 is displayed upon operating the selection button 70 in a selectable manner and in a state overlapped on the user page 56. Examples of information in the animal type list 72 are "LARGE" for a large dog or the like, "MEDIUM" for a medium size dog or the like, and "SMALL" for a small dog, cat or the like. In case any one of the types of the animals is selected in the animal type list 72, a body part list 73 is displayed in a selectable manner in place of the animal type list 72.

The body part list 73 indicates examples of body parts in a list form, inclusive of "THORAX", "ABDOMEN" and "HEAD". Incase any one of the body parts is selected in the body part list 73, an imaging direction list 74 is displayed in a selectable manner in place of the body part list 73. The imaging direction list 74 indicates examples of imaging directions in a list form, inclusive of "FRONT", "LATERAL" and "DIAGONAL". In the example in the drawings, the options of "LARGE", "THORAX" and "FRONT" are selected in the animal type list 72, the body part list 73 and the imaging direction list 74. Color of selected background portions of the animal type list 72, the body part list 73 and the imaging direction list 74 is changed, to clarify the selected background portion to the veterinarian D.

Figure 13:
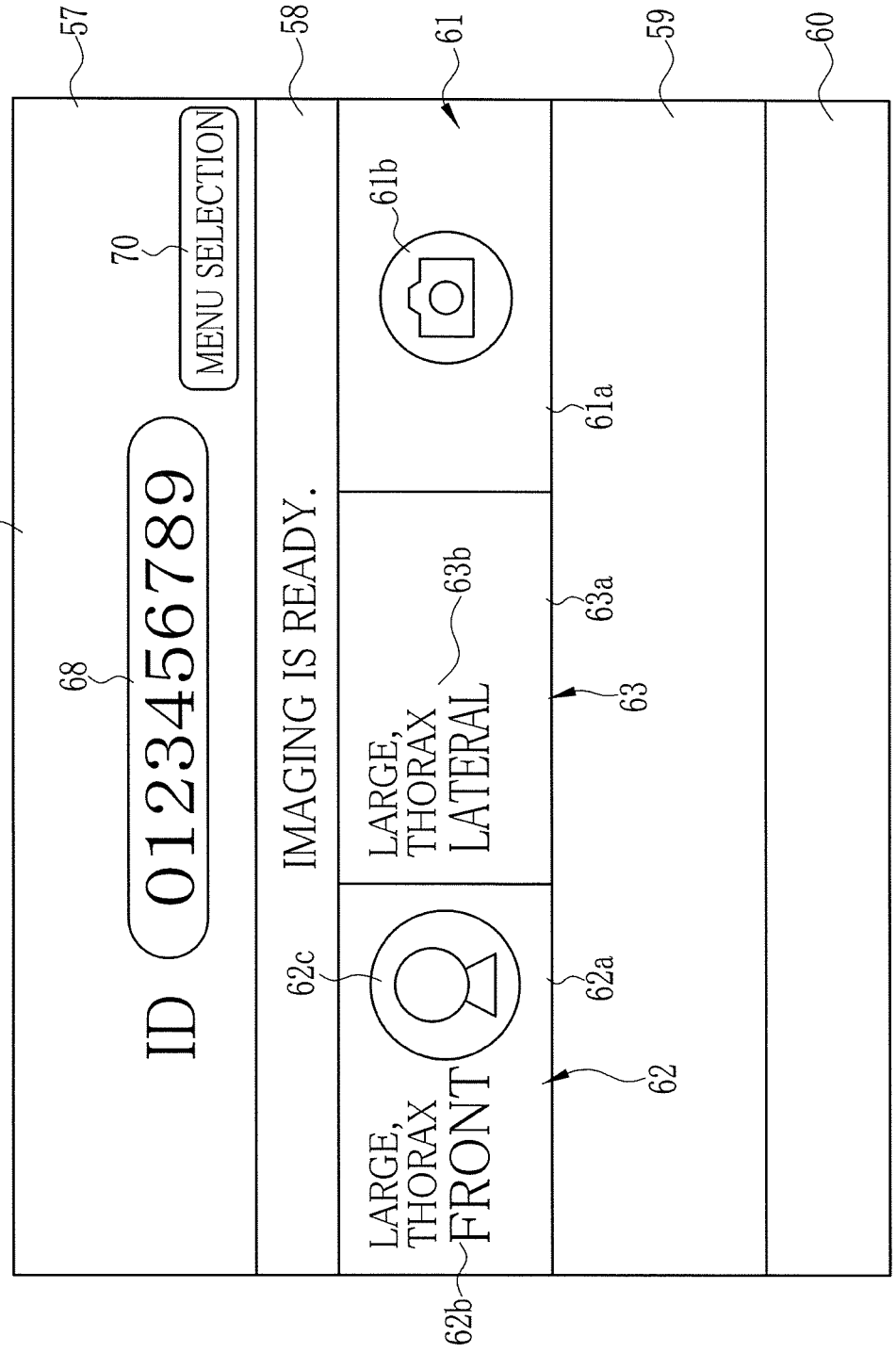
FIG. 13 is a plan illustrating the user page after the menu registration.

Upon selecting one of imaging directions from the imaging direction list 74, the first user menu structure 62 or 63 according to the selected animal type, body part and imaging direction is registered in the portable console device 31. The selected animal type, body part and imaging direction are added to the registered first user menu structure 62 or 63 as animal type information and imaging information. In FIG. 13, the first user menu structures 62 and 63 are displayed in the sample window area 59 in a manner visible simultaneously. The first user menu structures 62 and 63 respectively have the display area 62*a* and a display area 63*a* extending in a horizontally longitudinal quadrilateral form. The attribute information 62*b* and attribute information 63*b* or alphanumeric information is indicated in the display areas 62*a* and 63*a* for expressing the selected animal type, body part and imaging direction set upon the registration. An imaging icon 62*c* or indicator icon is displayed in one of the first user menu structures 62 and 63 in which a radiation image will be formed next. In the example depicted in the drawing, an example of the imaging icon 62*c* is in a symbolized form of a radiation source. Also, the display areas 62*a* and 63*a* are active input areas of the first user menu structures 62 and 63 for manual touch.

For example, the first user menu structure 62 is registered according to the animal type list 72, the body part list 73 and the imaging direction list 74 in FIG. 12. Letters of "LARGE", "THORAX" and "FRONT" are displayed in the display area 62*a* according to the animal type, body part and imaging direction set at the time of the registration.

In the processing of the radiation image acquisition, the portable console device 31 transmits animal type information and imaging information to the radiation image detector 30 according to a sequence of registering the first user menu structures 62 and 63. In case condition setting of the signal processing is terminated in the radiation image detector 30 according to the animal type information and imaging information, the portable console device 31 receives a ready signal from the radiation image detector 30. The display controller 42 upon receiving the ready signal causes the status display area 58 to display a message of "IMAGING IS READY".

The animal type information and imaging information of the first user menu structures 62 and 63 is transmitted to the radiation image detector 30 in a sequence of the registration. Imaging is performed according to the sequence of the transmission. However, a sequence of the imaging can be changed by selecting the first user menu structure 62 or 63 on the user page 56. For example, the first user menu structure 63 is selected while the imaging with the first user menu structure 62 is ready. The imaging icon 62c in the first user menu structure 62 is deleted, and the imaging icon 62c is displayed in the first user menu structure 63 instead. Also, the animal type information and imaging information of the first user menu structure 63 is transmitted to the radiation image detector 30, to perform condition setting of signal processing prior to the imaging.

The number of the first user menu structures 62 and 63 registered in the portable console device 31 is not limited to two. One or three or more of the user menu structures can be registered, for example, at the time of imaging of plural radiation images at one event of the image browsing. Assuming that the sample window area 59 cannot display all of the plural user menu structures simultaneously, then the sample window area 59 is set in a scrollable form, for a user to view all of the plural user menu structures by scrolling.

The second user menu structure 61 includes a display area 61a and an indicator icon 61b. The display area 61a is in a rectangular quadrilateral form and horizontally long. The indicator icon 61b is displayed within the display area 61a. A form of the indicator icon 61b is a figure in which optical imaging is symbolized. In the example depicted in the drawing, the indicator icon 61b is in a symbolized form of a camera. Also, the display area 61a is an operation area of the second user menu structure 61 for manual touch.

Figure 14:
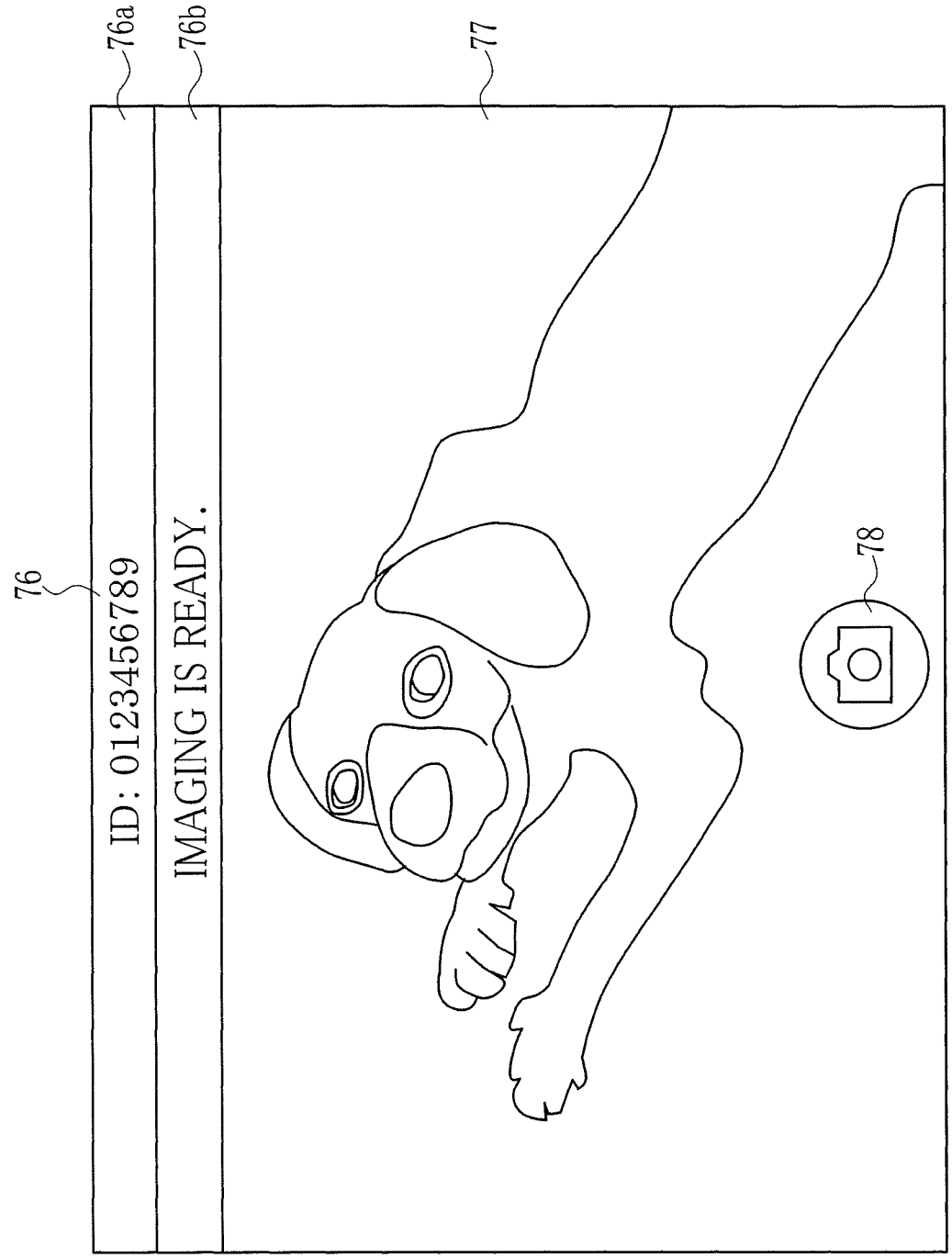
FIG. 14 is a plan illustrating a live image view.

The display controller 42, upon operation of the second user menu structure 61, changes over the touchscreen display unit 31a from the user page 56 to a live camera view 76 (live image view) for photographing an optical image of the animal body P as illustrated in FIG. 14. The optical camera unit 31b is started up to start photographing a live image of the animal body P. The live camera view 76 includes an image display area 77 and window areas 76a and 76b. The image display area 77 is a relatively large part of the live camera view 76. The window areas 76a and 76b are disposed higher than the image display area 77, and display information of the body ID and status information.

The image display area 77 displays a live image (live image view) of the animal body P photographed by the optical camera unit 31b. A shutter button 78 is disposed at a center of a lower portion of the image display area 77 for photographing the optical image of the animal body P. The live image is an image or moving image on the display before depressing the shutter button for photographing so as to check an angle of photography or object to be photographed, without recording to a recording medium or the like. The live image as moving image is displayed in the image display area 77.

In case the shutter button 78 is depressed in the live camera view 76, the optical camera unit 31b starts photographing an optical image of the animal body P. The display controller 42 changes over the touchscreen display unit 31a from the live camera view 76 to the user page 56. Also, the display controller 42 creates a small size image in a smaller size from the optical image.

Figure 15:
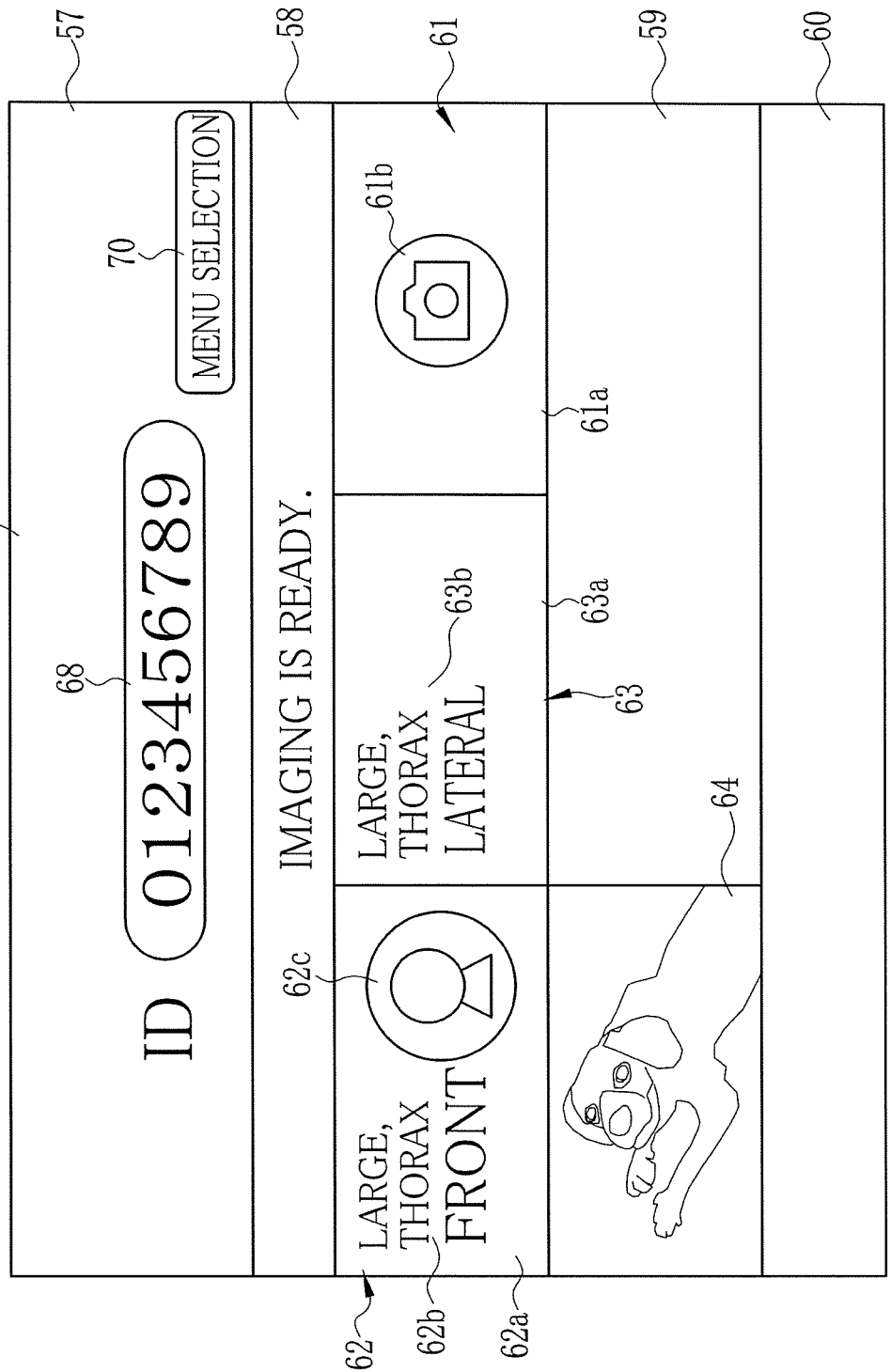
FIG. 15 is a plan illustrating the user page after displaying an optical image.

In FIG. 15, the optical image 64 of a reduced size is disposed in the sample window area 59 in such a manner that at least one portion of the animal body P with visual distinction is not overlapped on the second user menu structure 61. In the drawing, the sample window area 59 has a sufficient space. The optical image 64 is displayed in the same size as the second user menu structure 61 without overlap on the second user menu structure 61.

Figure 16:
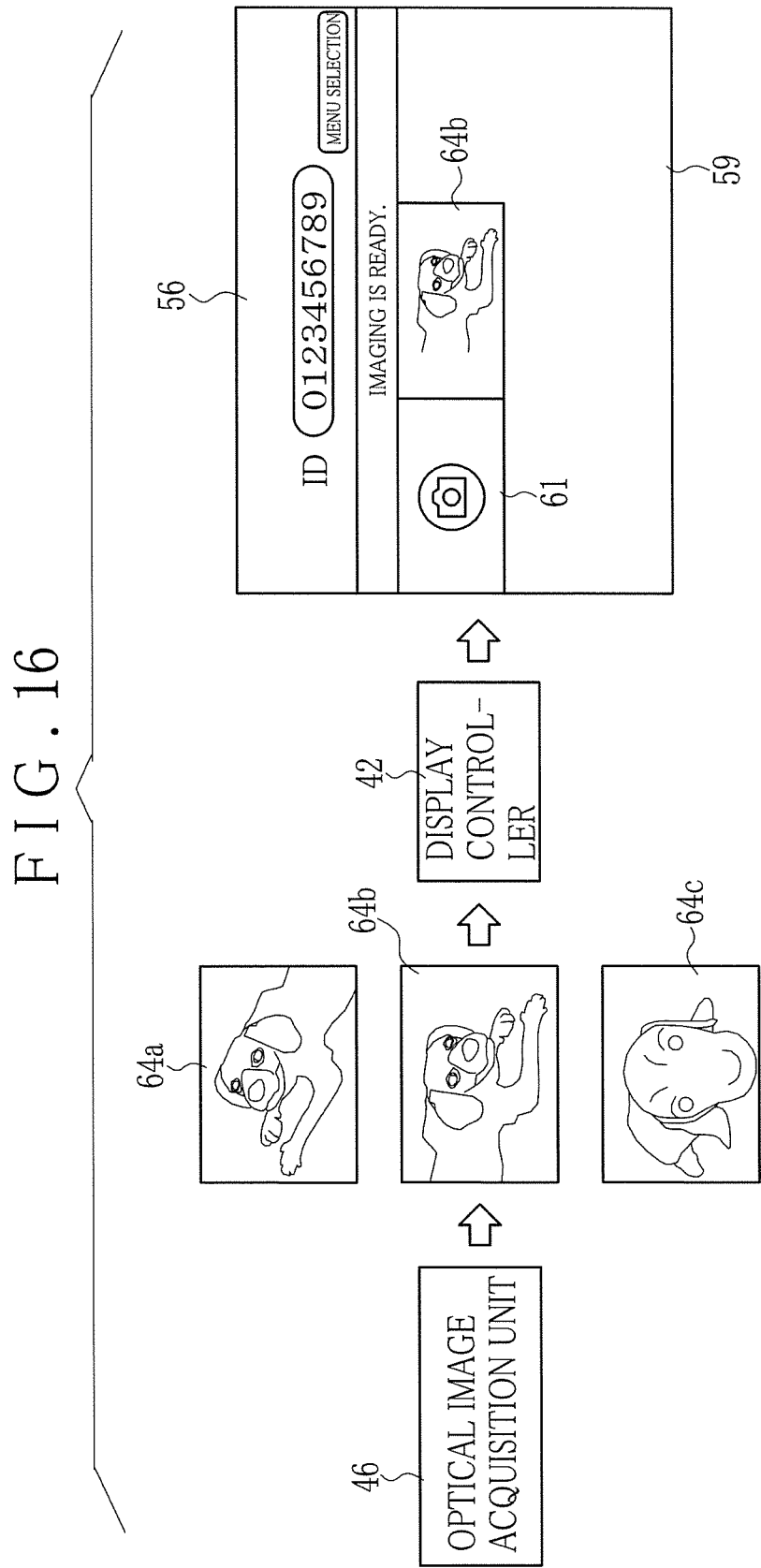
FIG. 16 is an explanatory view illustrating a rule for use upon acquiring plural optical images.

Assuming that three optical images 64a, 64b and 64c are photographed by the optical camera unit 31b as illustrated in FIG. 16, a space for displaying the first user menu structure 62 or the second user menu structure 61 may be considerably narrowed by simultaneous display of all of the optical images 64a-64c in the sample window area 59. In consideration of preventing such a problem, the display controller 42 performs display control of displaying a selected one of the optical images 64a-64c in the sample window area 59, for example, the optical image 64a.

To select optical images to be displayed in the sample window area 59, any one of plural selecting methods can be used. For example, an optical image in which the animal body P can be distinguished most easily by face recognition or image recognition. Also, one of plural optical images photographed at the first time can be selected. Furthermore, it is possible to change over and display the plural optical images upon lapse of predetermined time one after another. Should the first user menu structure 62 not registered further and should an unused space remain in the sample window area 59, then the plural optical images can be displayed in the unused space.

Figure 17:
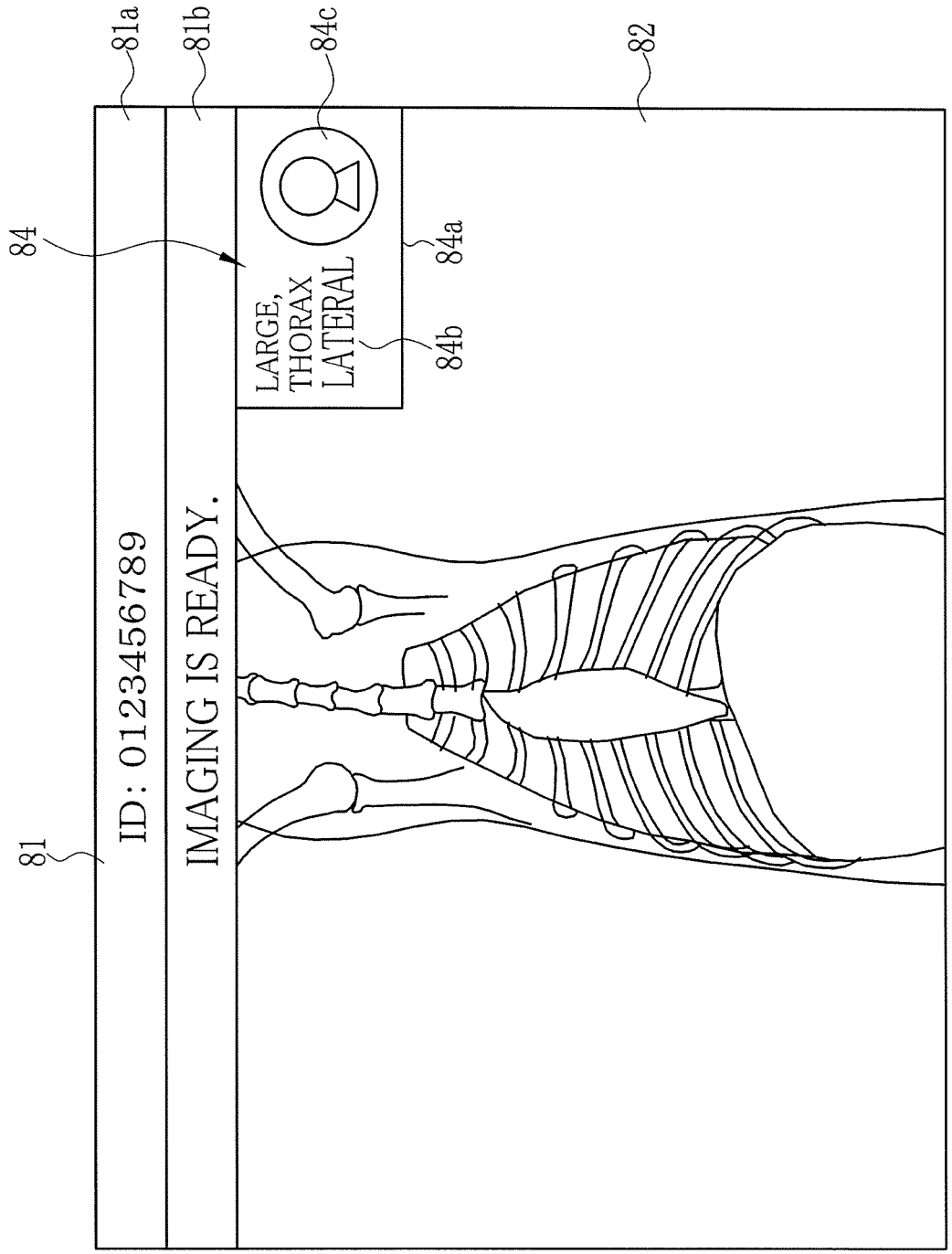
FIG. 17 is a plan illustrating a view page.

The radiation image acquisition includes a step of receiving a radiation image from the radiation image detector 30, and a step of displaying the radiation image on the touchscreen display unit 31a. Upon receiving the radiation image in the portable console device 31, the display controller 42 changes over the touchscreen display unit 31a from the user page 56 to a view page 81 or image screen for displaying the received radiation image of the animal body P as illustrated in FIG. 17. The view page 81 is used for acquisition of radiation images and aid in explaining radiation images to an animal owner, and includes an image display area 82 of a large form, and window areas 81a and 81b disposed higher than the image display area 82 for indicating a body ID and status information. The image display area 82 displays the received radiation image. Also, the view page 81 is changed over in the user page 56 in case the first user menu structure 62 or 63 is touched continuously at least for a predetermined period, namely, by long press. Assuming that the first user menu structure 62 or 63 before imaging is touched by long press for changeover to the view page 81, the image display area 82 does not display any item. However, assuming that a radiation image is received, the image display area 82 displays the received radiation image.

A succeeding first user menu structure 84 or radiographic imaging menu structure is displayed in a right upper portion of the image display area 82 in a manner overlapped on a radiation image. The succeeding first user menu structure 84 is a menu related to a succeeding radiation image next to the presently displayed radiation image in the image display area 82. The succeeding first user menu structure 84 includes a frame line 84a, attribute information 84b or alphanumeric information, and an imaging icon 84c or indicator icon. The frame line 84a divides the display area. The attribute information 84b represents an animal type, body part and imaging direction of a succeeding radiation image. The imaging icon 84c is substantially the same as the imaging icon 62c. In the drawing, a radiation image formed according to the first user menu structure 62 is displayed in the image display area 82. The succeeding first user menu structure 84 in the image display area 82 corresponds to the first user menu structure 63.

Figure 18:
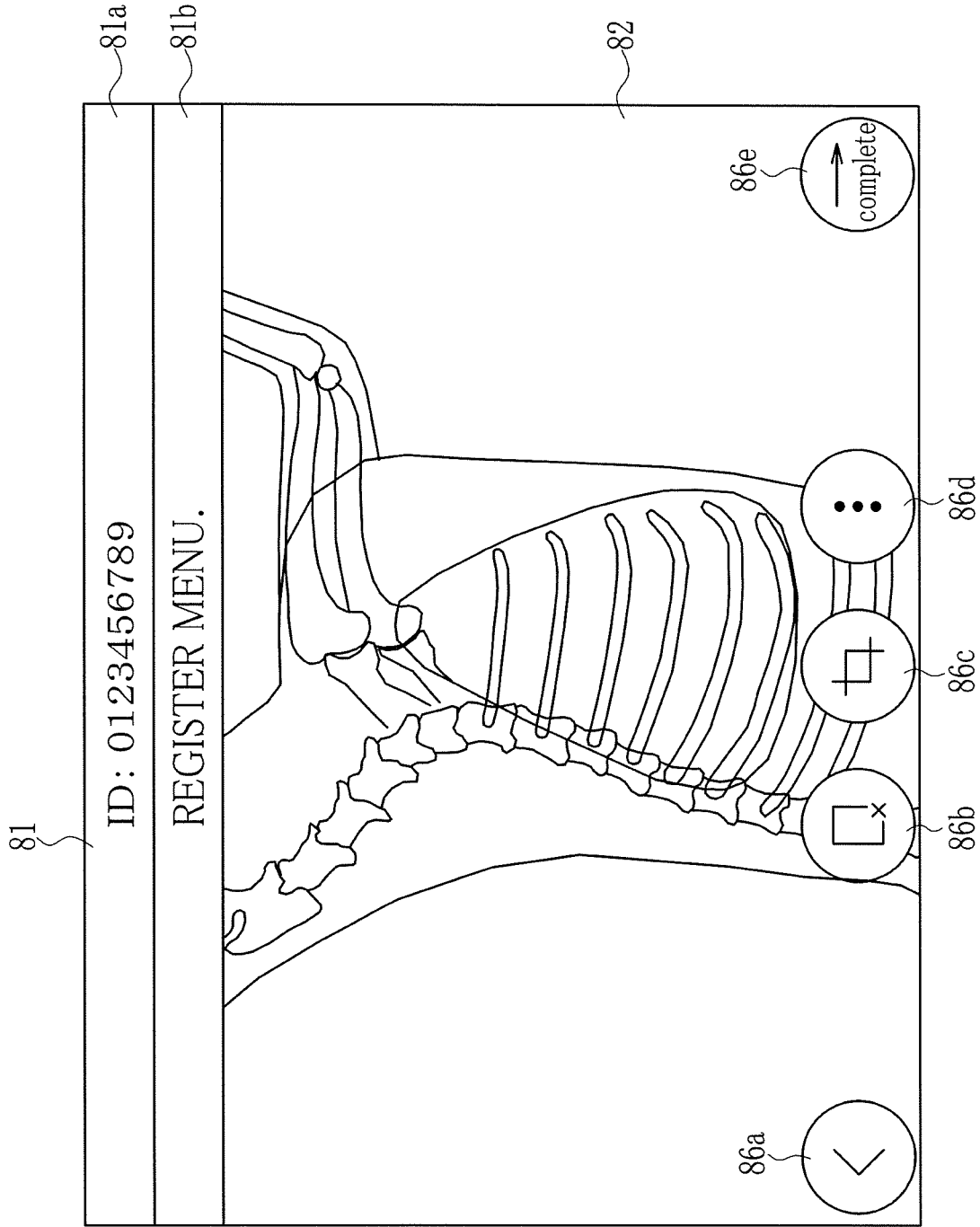
FIG. 18 is a plan illustrating the view page with an input button.

Upon imaging according to the succeeding first user menu structure 84, the image display area 82 displays a radiation image formed according to the succeeding first user menu structure 84 as illustrated in FIG. 18. Note that the imaging of the succeeding first user menu structure 84 can be performed while the view page 81 is displayed or after changeover from the view page 81 to the user page 56. However, it is preferable to perform the imaging with the view page 81 assuming that imaging of plural radiation images is desired from a position distant from the veterinarian D or operator and with changes in the posture of the animal body P between events of imaging, as illustrated in FIG. 2. It is possible by use of the view page 81 to check the image even from a distant position, as the radiation image becomes displayed in a large size. Also, it is possible to change the posture of the animal body P according to the succeeding first user menu structure 84, because the succeeding first user menu structure 84 is displayed in the view page 81.

In case a flicking action on the image display area 82 is performed by touch of a finger moving quickly, the display controller 42 changes over the radiation image on the image display area 82. For example, upon flicking on the image display area 82 to a right side, a past radiation image acquired formerly before the displayed present radiation image is displayed in the image display area 82. Also, upon flicking on the image display area 82 to a left side, a new radiation image acquired after the displayed radiation image is displayed in the image display area 82.

Also, performing a flicking action to the succeeding first user menu structure 84 can change a sequence of imaging of radiation images by changing over user menus in the image display area 82. For example, the succeeding first user menu structure 84 can be flicked while imaging of the succeeding first user menu structure 84 is set ready. Then the succeeding first user menu structure 84 is deleted. Still another first user menu structure for planned subsequent imaging is displayed as a new first user menu structure.

Upon touching the image display area 82 in the view page 81, various buttons become displayed under the image display area 82, including a changeover button 86*a*, an exclusion button 86*b* or turn-off button, a trimming button 86*c*, a comment button 86*d* and an end button 86*e*. The changeover button 86*a* is operated to change over the view page 81 to the user page 56. Upon operating the changeover button 86*a*, the display controller 42 changes over the touchscreen display unit 31*a* from the view page 81 to the user page 56. The exclusion button 86*b* is used for setting a radiation image as an excluded image without use for image browsing. Upon operating the exclusion button 86*b*, a radiation image displayed in the image display area 82 is set as an excluded image. In the user page 56, a first user menu structure is automatically registered with the same animal type information and imaging information as the excluded image.

The trimming button 86*c* is used for trimming of a radiation image. Upon depressing the trimming button 86*c*, a quadrilateral trimming frame (not shown) is indicated in the image display area 82. A position and size of the trimming frame is adjusted, to input a command signal for trimming. Then a portion of the radiation image outside the trimming frame is deleted. The comment button 86*d* is used for adding comment to the radiation image. Upon depressing the comment button 86*d*, a comment screen view and a software keyboard are displayed to overlap on the view page 81, the software keyboard being for inputting comment into the comment screen view. The input comment in the comment screen view is recorded as metadata of the radiation image. The end button 86*e* is used for instructing termination of image browsing in a manner similar to the end button 69 described above. Upon depressing the end button 86*e*, the portable console device 31 transmits the radiation image and optical images of the animal body P to the image server 12, and stores the same in the image server 12. In the user page 56, the body ID is deleted, to enable image browsing of next animal body.

Figure 19:
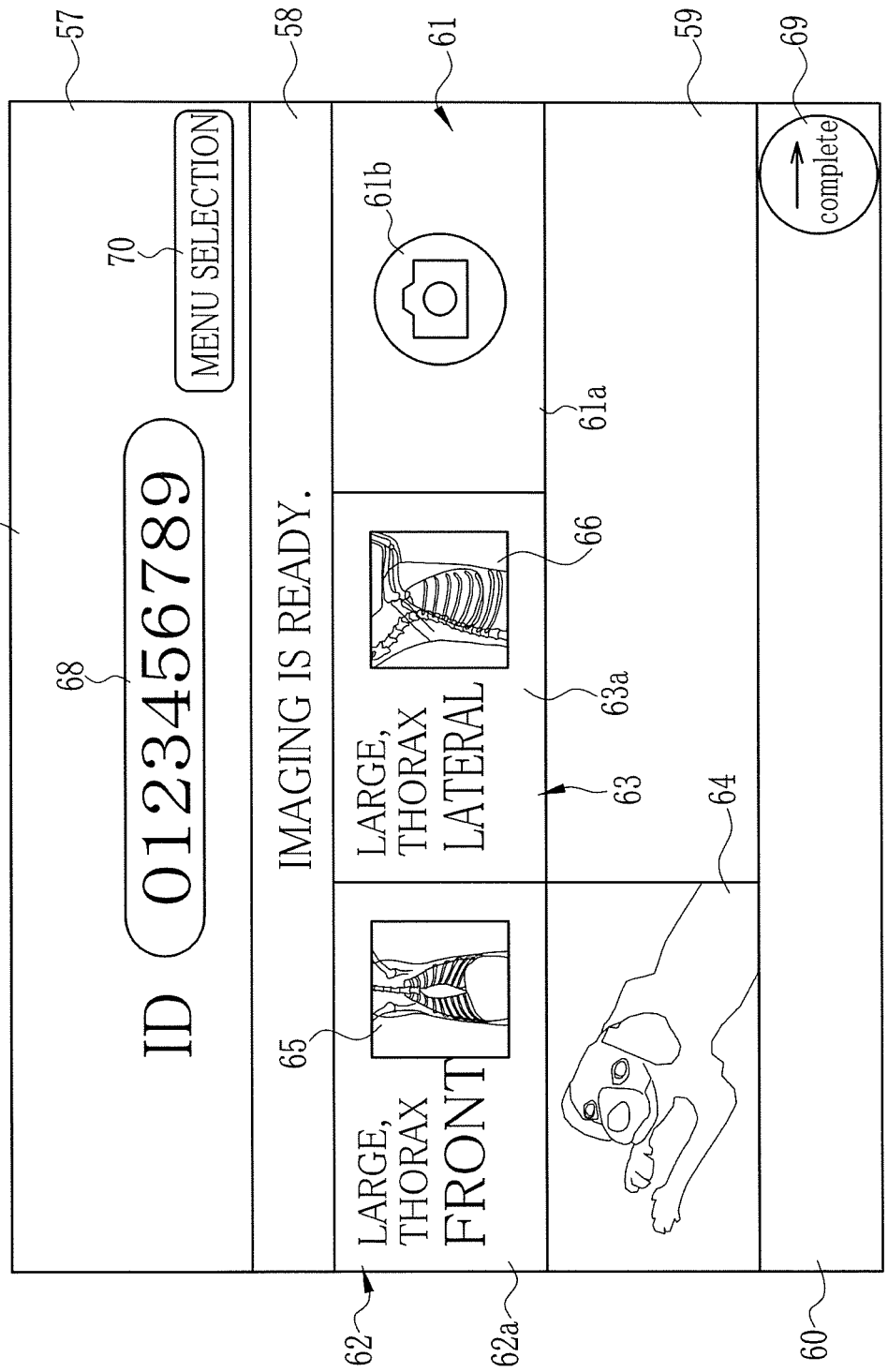
FIG. 19 is a plan illustrating the user page after displaying a radiation image.

In FIG. 19, changing over the touchscreen display unit 31*a* from the view page 81 to the user page 56 after radiographic imaging displays the sample window area 59 with the radiation images 65 and 66 in a reduced shape in a list form. The radiation images 65 and 66 are displayed in such a smaller size than the optical image 64 that a sufficient display space is formed within the sample window area 59 and that at least one of the optical images 64 is displayed in a larger size than the radiation images 65 and 66. In the depicted example, the radiation images 65 and 66 are displayed in an overlapped manner with the display areas 62*a* and 63*a* of the first user menu structures 62 and 63.

In case the radiation image 65 or 66 in the user page 56 is depressed for long press, the display controller 42 changes over the touchscreen display unit 31*a* from the user page 56 to the view page 81, to display a selected radiation image selected in the image display area 82 in a large size. The formed radiation image is displayed even after return to the user page 56, so that a veterinarian can utilize the radiation image for explanation to the animal owner. Note that the size of the radiation image herein is an area of display of the radiation image.

Figure 20:
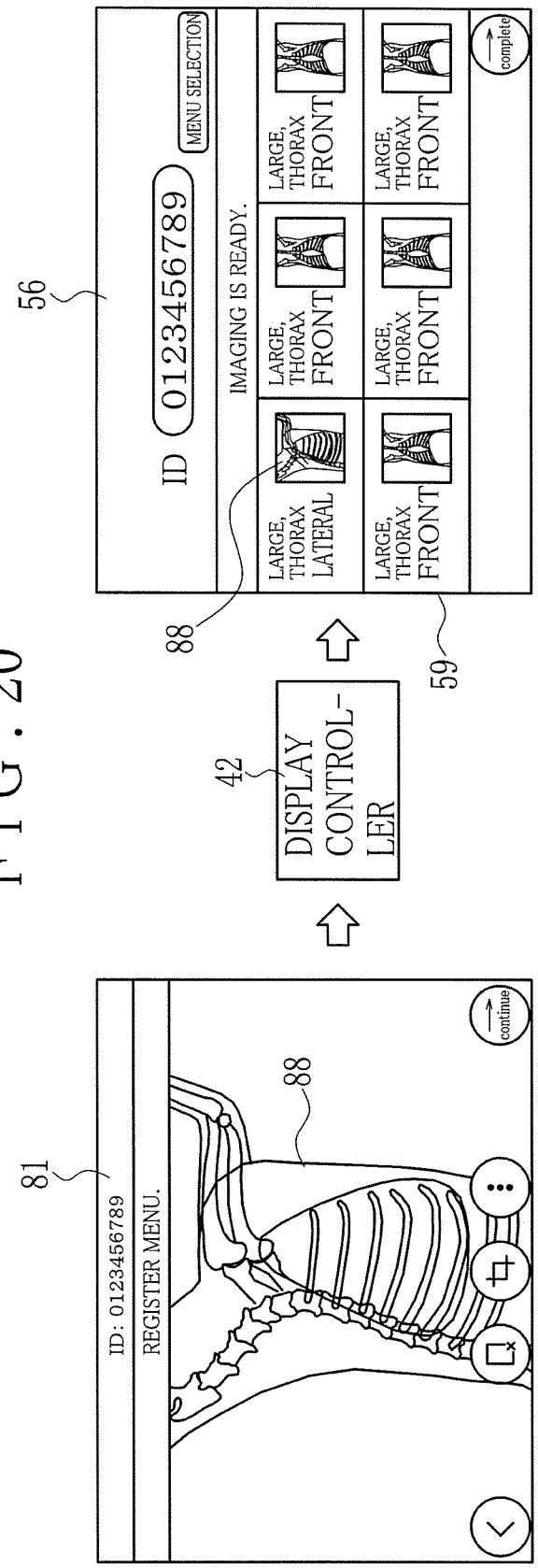
FIG. 20 is an explanatory view illustrating changeover from the view page to the user page.

Let a plurality of first user menu structures be registered. Let the sample window area 59 be set in a scrollable state. Assuming that a return to the user page 56 is desired after checking a given radiation image in the view page 81, a problem of not easily finding a succeeding radiation image will occur in the absence of a radiation image viewed in the view page 81 from the user page 56. To solve such a problem, the display controller 42 in FIG. 20 performs display control to display the radiation image on the user page 56 as the same image checked in the view page 81 at the time of changeover from the view page 81 to the user page 56. In the drawing, a radiation image 88 of the thorax on a lateral side is illustrated. The radiation image 88 having been displayed in the view page 81 for the thorax and the lateral side becomes displayed in the sample window area 59 of the user page 56 upon changeover from the view page 81 to the user page 56. This is effective in improving efficiency in the image browsing, as the image to be checked next can be recognized in the user page 56.

Figure 21:
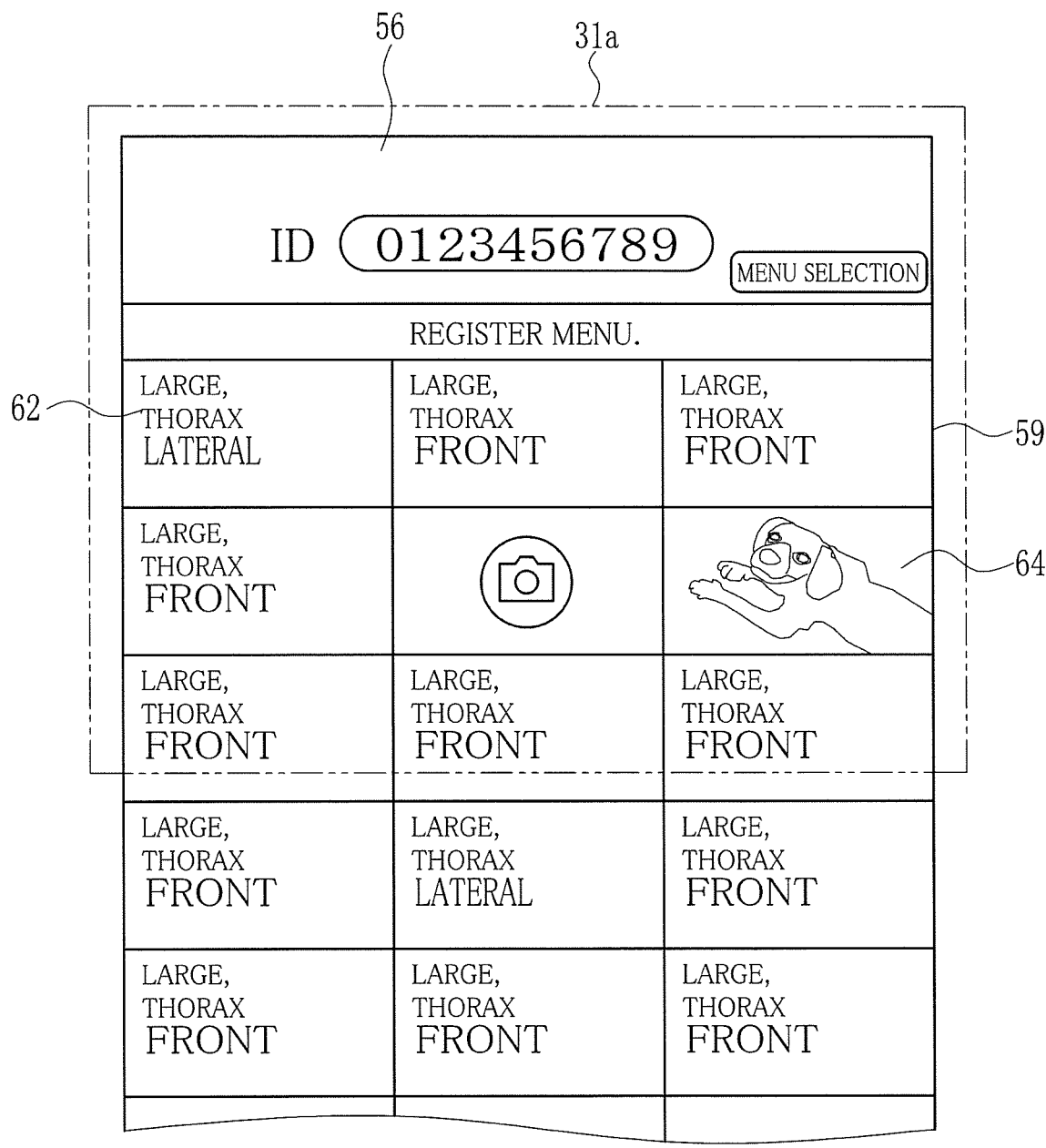
FIG. 21 is a plan illustrating a rule for displaying a scrollable user page.

In FIG. 21, a great number of user menus are registered. The sample window area 59 in the user page 56 is displayed in a scrollable manner. Then the display controller 42 performs the display control for displaying the optical image 64 of the animal body P unfailingly irrespective of a position of scroll of the sample window area 59. It is therefore possible to display the optical image 64 of the animal body P no matter where the sample window area 59 is scrolled. Errors in identifying the animal body P in the image browsing can be prevented. Also, the image browsing can be performed efficiently, as no scroll of the sample window area 59 is required for checking the optical image 64.

Upon selecting the image viewing mode in the main page 51, receiving the ID is processed in the same manner as the image browsing mode. Then the optical image acquisition unit 46 and the radiation image acquisition unit 47 acquire a radiation image and optical image from the image server 12 in correspondence with the body ID. The display controller 42 displays a review page (not shown) or tracking page on the touchscreen display unit 31a substantially in the same form as the user page 56. In the review page, the optical image is displayed without overlapping on the second user menu structure (optical imaging menu structure). The radiation image is displayed with at least one portion overlapped on the first user menu structure. Upon selection of the radiation image in the review page, the touchscreen display unit 31a is changed over from the review page to a view page (not shown) substantially in the same form as the view page 81. The selected radiation image is displayed in a large size. Thus, past radiation images can be viewed.

As described heretofore, at least one optical image 64 of the animal body P in the embodiment is displayed in the sample window area 59 in the user page 56 in a larger size than the radiation image of the animal body P. Thus, the animal body P can be viewed and confirmed properly by improved recognition of the optical image 64. Also, a display space in the sample window area 59 can be sufficient as the radiation image 65 is displayed in a smaller size than the optical image 64. The first and second user menu structures 61 and 62 can be displayed largely and with good operability.

It is also possible to utilize the portable console device 31 for obtaining an optical image of the animal body P and for aid in explaining the radiation image to an animal owner, because a size of the portable console device 31 is suitable for portability and easy handlability in veterinary use. A size in the alphanumeric information in the touchscreen display unit 31a and a size of an input field of the menu structure are set suitably for the veterinary use. It is possible to prevent errors in reading the alphanumeric information or errors in operating the menu structure. Operability and recognition of the menu can be improved.

In the present embodiment, the examples of the second user menu structure 61 and the first user menu structure 62 have attribute information (alphanumeric information), indicator icons or the like in the predetermined display area. However, a second user menu structure and a first user menu structure can have only the attribute information 62b or 63b or the indicator icon 61b. Thus, numerous variations of forms of the second user menu structure 61 and the first user menu structure 62 can be utilized. It is possible to display user menus suitable for the size of the touchscreen display unit, even though the size of the touchscreen display unit in the console device is small.

Figure 22:
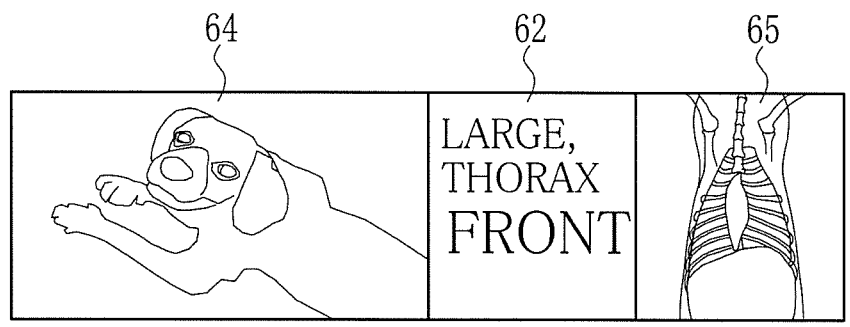
FIG. 22 is a plan illustrating other preferred first and second user menu structures.
Figure 23:
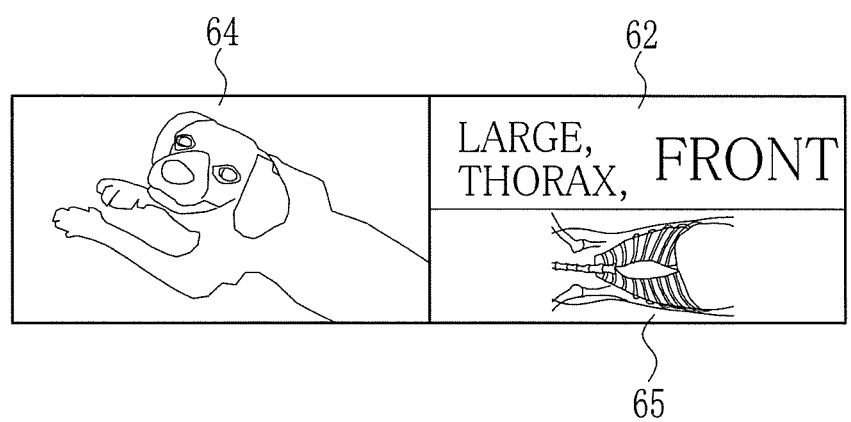
FIG. 23 is an explanatory view illustrating still another preferred first user menu structure.

In the embodiment, the radiation image 65 is overlapped with the display area 62a of the first user menu structure 62. In FIG. 22, another preferred embodiment is illustrated, in which the radiation image 65 is displayed adjacently with the first user menu structure 62. It is preferable to contain the first user menu structure 62 and the radiation image 65 in a display area of a size equal to that of the optical image 64, in the arrangement of the radiation image 65 adjacent with the first user menu structure 62. A display size is equal between the second user menu structure 61, the optical image 64, the first user menu structure 62 and the radiation image 65, which can be easily arranged in the sample window area 59. Note that the first user menu structure 62 and the radiation image 65 can be arranged vertically on upper and lower sides as illustrated in FIG. 23 instead of the horizontal arrangement. Preferably, the first user menu structure 62 and the radiation image 65 can be adjacent with one another to be contained in a display area of the size of the optical image 64. Furthermore, the size of the display area of the first user menu structure 62 and the radiation image 65, which is exactly equal to that of the optical image 64 in the drawing, can be approximately equal to that of the optical image 64. A size of the display area of the first user menu structure 62 and the radiation image 65 should be so determined that no gap between the first user menu structure 62 and the radiation image 65 is formed within the sample window area 59.

Figure 24:
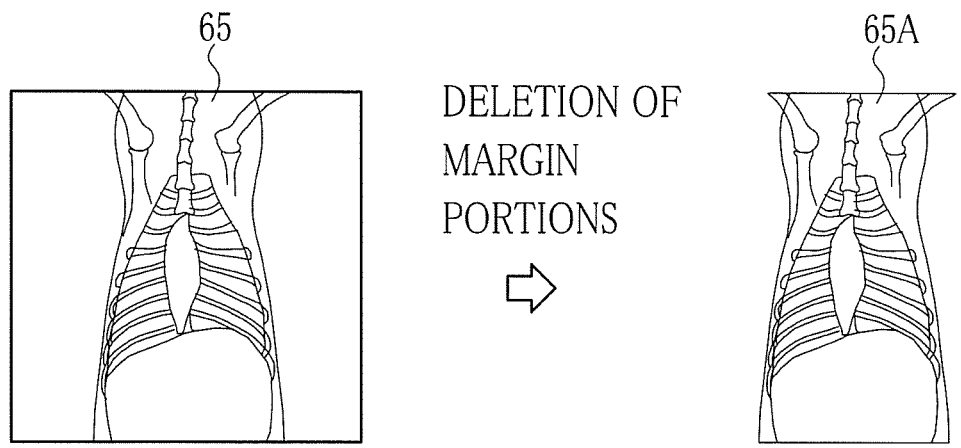
FIG. 24 is an explanatory view illustrating a modified radiation image created by deleting margin portions from a radiation image.

In the present embodiment, the radiation image 65 is displayed in the user page 56 in the reduced size. However, the radiation image 65 of too small a size cannot be recognized appropriately. In FIG. 24, a preferred embodiment is illustrated, in which margin portions are deleted from the radiation image 65 around an object area of the animal body P (background erasing), to form a modified radiation image 65A. It is possible to reduce a size of the radiation image 65A and display the radiation image 65A in the sample window area 59. The object area of the animal body P can be displayed in a larger size than that in the radiation image 65 having the margin portions. Thus, recognition of the radiation image 65A in the user page 56 can be highly improved.

Figure 25:
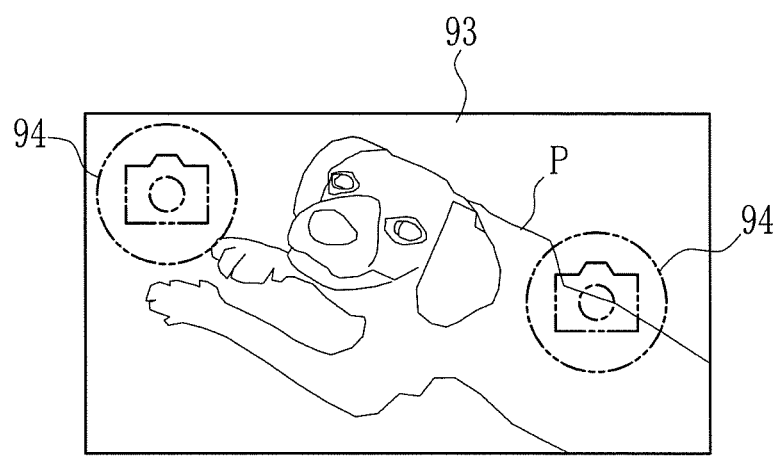
FIG. 25 is an explanatory view illustrating another preferred second user menu structure.

In the above embodiment, the optical image 64 does not overlap with the second user menu structure 61. In FIG. 25, another preferred embodiment is illustrated, in which a peripheral portion in an optical image 93 (identification image) is displayed to overlap with a second user menu structure 94 or optical imaging menu structure which is an icon. An example of the peripheral portion is a portion without use for checking the animal body P, such as a portion other than a face of an animal, a background portion behind the animal body P, and the like. It is therefore possible to utilize a display space effectively without influencing to recognition of the animal body P in the optical image 93. Note that the peripheral portion in the optical image 93 not for use in checking the animal body P can be processed by image processing for visual distinction, for example, for face recognition, background recognition or the like in the optical image 93.

Other preferred embodiments of the invention are hereinafter described. Elements similar to those of the first embodiment are designated with identical reference numerals.

Second Embodiment

Figure 26:
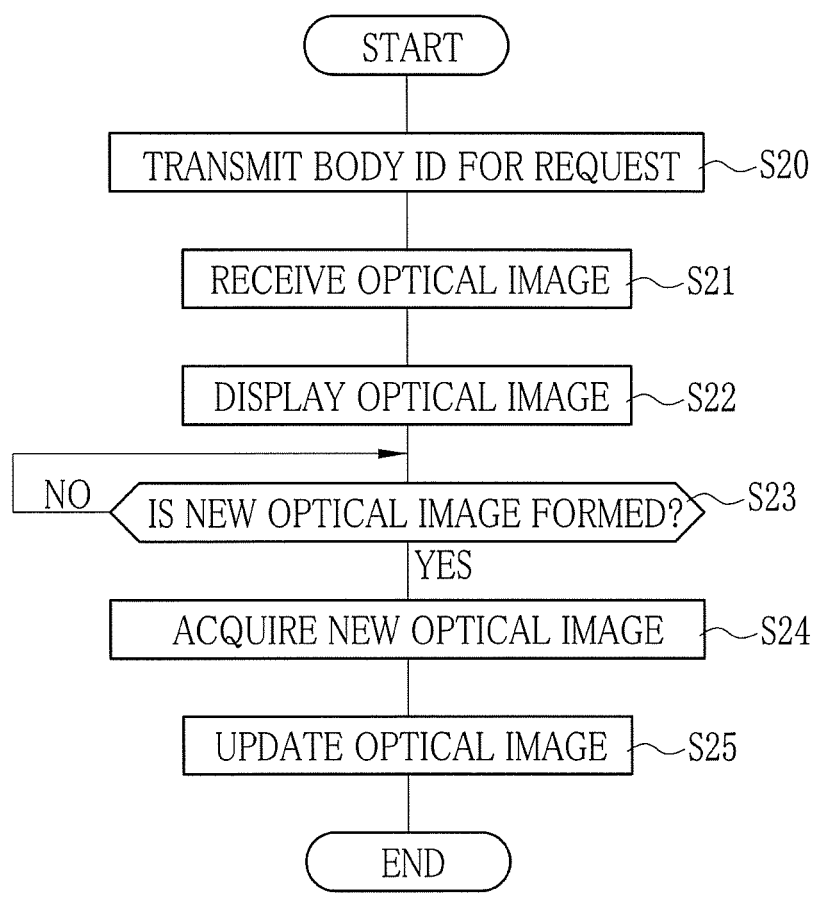
FIG. 26 is a flow chart illustrating optical image acquisition in a second preferred embodiment.
Figure 27B:
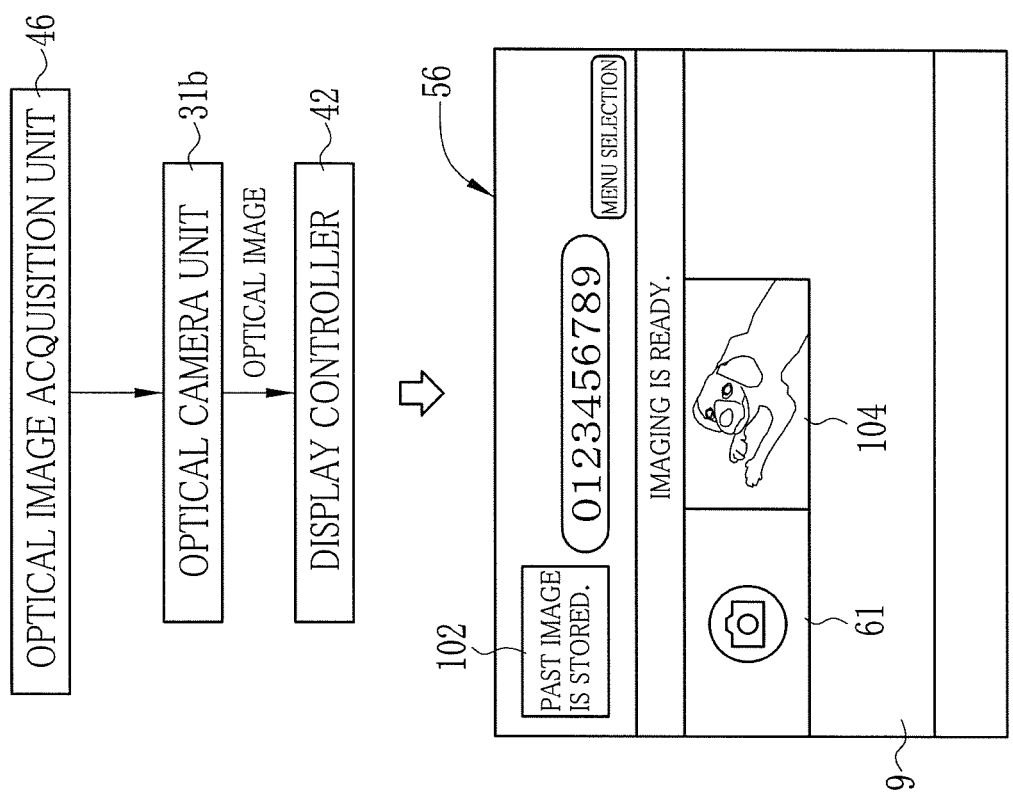
FIGS. 27A and 27B are explanatory views illustrating the optical image acquisition in a second preferred embodiment.
Figure 27A:
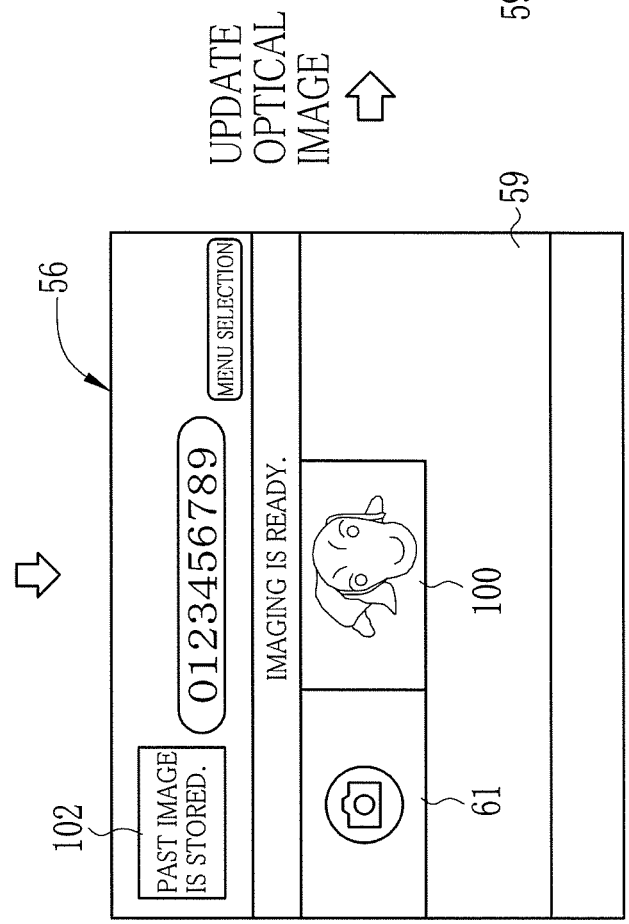

In the first embodiment, an optical image from the optical camera unit 31b is displayed in the user page 56. In a second embodiment, in contrast, a past optical image is acquired from the image server 12 according to a past event of veterinary care. The user page 56 displays the past optical image. In FIGS. 26, 27A and 27B, the optical image acquisition unit 46 transmits a request of distribution to the image server 12 for an image together with a body ID received by the ID reception in the step S20. In the portable console device 31, an optical image 100 (identification image) searched from the optical image database 34 according to the body ID is received from the image server 12 in the step S21. The display controller 42 causes the user page 56 to display the optical image 100 being received, in the step S22.

Thus, the optical image 100 of the animal body P can be checked on the portable console device 31 even without newly forming an optical image of the animal body P. Also, the animal of the animal body currently present in the veterinary clinic can be readily identified with the animal of an animal body of a former case by displaying and checking the past optical image of the former case in the user page 56. In general, each one animal owner can have plural animals as pets in the trends of animal breeding as a hobby. Also, one animal owner may have an animal of the same type as that which was bred by him or her but is not alive now. Some animal owner may give a new animal the same name as that bred formerly. Furthermore, a great number of animals may be bred collectively in agricultural industry, for example, in pig farming, poultry farming and the like. The feature of the present invention of identifying the animal body with that of the past optical image can be effective in the image browsing without error in identifying the animal body of the animal, particularly among plural animals bred by a single animal owner.

Also, it is possible at the time of requesting distribution of an optical image to the image server 12 to transmit a request of search (search query) to the image server inclusive of the body ID, to check presence or absence of a radiation image in the radiation image database 33 in correspondence with the body ID. To this end, the radiation image acquisition unit 47 corresponding to a radiation image searcher sends the request of search (search query) to the image server. Assuming that a past radiation image exists in correspondence with the animal body ID, a message 102 (message information) of "PAST IMAGE IS STORED" is displayed in the user page 56. This is effective in notifying information of medical history of the past image browsing without reviewing a medical chart or other records. Furthermore, the radiation image itself can be displayed after confirming the presence, in place of the message 102 as information of the presence of the radiation image.

In case a new optical image is photographed by operation of the second user menu structure 61 (yes in the step S23) with necessity of the new optical image after aging of the animal body P, then the optical image acquisition unit 46 acquires an optical image 104 (identification image) from the optical camera unit 31b in the step S24. The display controller 42 replaces the optical image 100 in the user page 56 with the optical image 104 obtained newly in the step S25. Thus, the optical image with which the animal body P can be recognized can be displayed in the user page 56 according to the present condition of the animal body P.

Third Embodiment

In the second embodiment, the optical image 100 from the image server 12 is replaced with the optical image 104 newly photographed by the optical camera unit 31b. In FIG. 28, a third preferred embodiment is illustrated, in which the optical images 100 and 104 are displayed together in the sample window area 59. Also, a status icon 106 (information of graphic expression) can be displayed in an overlapped manner with the optical images 100 and 104 for indicating other undisplayed optical images. Furthermore, it is possible to enlarge and display the optical images 100 and 104 upon manual touch to areas of the optical images 100 and 104. Thus, the use of the optical images can be effective not only for identifying the animal body P but also for medically observing a lesion of injury or skin disease. Note that letters or other graphical expression can be used for indicating other undisplayed optical images in place of the icon.

Fourth Embodiment

In the above embodiments, diagnostic information including radiation images and optical images of an animal body is managed according to the body ID. In a fourth embodiment, an owner ID is issued for an animal owner to be discerned. Diagnostic information of an animal body is managed according to the owner ID. Each one of the animal owners is likely to have a plurality of animals. Thus, it is preferable to issue sub IDs associated with animal bodies in combination with the owner ID. Diagnostic information of each of the animal bodies can be managed according to the sub IDs.

In FIG. 29, an image database 110 is illustrated and used for managing optical images and radiation images of animal bodies according to the owner ID and the sub ID. The owner ID is issued for an animal owner of the animal. The sub ID is issued according to the owner ID. For example, an owner ID of 0123456 is assigned to an animal owner A (not shown). A sub ID of 0123456-JOHN is assigned to a dog John owned by the animal owner A, as a combination of the owner ID and the name of the animal. An optical image 111 (identification image) and a radiation image 112 of John are associated with the sub ID of 0123456-JOHN, and managed by the date and time of the image browsing.

Let the animal owner A have a cat newly, with a name Tama (or Kitty or the like). In case he or she comes to the veterinary clinic with Tama for the first time, the veterinary D visually compares Tama with the optical image of John displayed in the user page 56, and recognizes the first visit of Tama. Then a sub ID of 0123456-TAMA is newly issued according to the owner ID of the animal owner A and a name of the cat owned newly. An optical image 113 (identification image) and a radiation image 114 of the cat can be managed by use of the image database 110 according to the sub ID.

Consequently, the management of diagnostic information of the body of the animal according to the owner ID of the animal owner clarifies a relationship between the animal owner and the body of the animal. Errors in identifying the body can be preferred even though the animal owner has a plurality of animals at the same time. The number of data of the IDs can be smaller than the number of data of the IDs in the management by use of body IDs, so that the management of the information can be facilitated.

Fifth Embodiment

In the third and fourth embodiments, the sub ID for the animal is issued according to the owner ID. However, the optical image of the animal itself can be utilized as recognition information by omitting the sub ID. In FIG. 30, a fifth embodiment is illustrated, in which an image database 120 is used to manage an optical image and radiation image of an animal body according to the owner ID assigned to the owner. In a manner similar to the third embodiment, the owner ID of 0123456 is assigned to an animal owner A (not shown). Optical images 121 and 122 (identification images) and radiation images 123 and 124 of John the dog and Tama the cat owned by the owner A are managed by the date and time of the image browsing in association with the owner ID.

In case the animal owner A comes to the veterinary clinic to input the owner ID of the animal owner A to the ID input field 68 of the portable console device 31, the optical images 121 and 122 of John and Tama in a recent date in FIG. 31 are read out from the image database 120, and displayed in the user page 56. A veterinarian D or operator selects the optical image 121 or 122 by use of those as visual recognition information, so that an animal body for image browsing in the event of veterinary care can be designated at the portable console device 31.

Upon selecting the optical images 121 and 122 in the user page 56, the message 102 can be displayed for presence or absence of a past radiation image corresponding to the selected optical images, or the past radiation image itself can be displayed. Also, it is possible to store relevancy information to the image database 120, the relevancy information expressing relevancy between the displayed radiation images after selecting the optical images 121 and 122 and radiation image of the image browsing in the present veterinary care of the animal. It is possible to read out radiation images of the relevancy according to the relevancy information. Consequently, a progress of the animal can be checked by reading out the radiation images of the same animal body even without managing the diagnostic information for each body ID. Furthermore, it is possible to display optical images at the newest image browsing in the user page 56 according to the date and time of the image browsing in response to an input of the owner ID of the animal owner A to the portable console device 31. This is effective in suitably utilizing a screen space in the sample window area 59 of the user page 56.

Thus, it is possible correctly to manage diagnostic information of the animal body as the optical images of the animal body associated with the owner ID is used as visual recognition information of each of the animal bodies. It is unnecessary to input the body ID or sub ID, so labor for managing the diagnostic information of the animal body can be saved.

Sixth Embodiment

The portable console device 31 in the first embodiment is disposed on the patient table 22 of the stand device 15 or a support plate near to the stand device 15. In FIG. 32, another preferred radiographic imaging system 130 is illustrated. A console holder 131 is disposed in the stand 20 of the stand device 15 for receiving insertion of the console housing of the portable console device 31 for positioning near to the control panel 25a of the source driver 25. This is effective in facilitating visual recognition of the portable console device 31 as the portable console device 31 is held on the portion of the stand device 15. Also, the portable console device 31 and the control panel 25a can be manually operated without leaving from the stand device 15, because the portable console device 31 is set near to the control panel 25a. Note that the nearness to the control panel 25a means such a distance that a veterinarian D can manipulate both of the portable console device 31 and the control panel 25a while he or she manually touches the animal body P without leaving. For example, a distance of the portable console device 31 from the control panel 25a can be equal to or less than 50 cm.

In the above embodiments, the basis of the portable console device 31 is the tablet terminal device. However, a basis of the portable console device 31 in the invention can be a notebook personal computer, smart phone, and other user terminal devices. In the above embodiments, the portable console device 31 is for the veterinary use. However, the portable console device 31 of the invention can be used for medicine for human patients, for example, emergency medicine.

In the above embodiments, the console device acquires radiation images from the radiographic imaging device having the FPD. However, a console device can acquire radiation images from other apparatuses or data sources, such as X-ray film scanner or IP reading device for use with an X-ray film, IP cassette, or the like.

According to a preferred embodiment mode of the invention, a computer-executable program for a portable information terminal device for acquiring a radiation image of a body created by a radiographic imaging device is provided. A program code is for display processing of the radiation image in a user page on a display unit. A program code is for display processing of at least one optical image of the body in the user page on the display unit in a larger size than the radiation image.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A console device of a portable type for acquiring a radiation image of a body created by a radiographic imaging device, comprising:
 a display device;
 a processor, configured to:
  transmit a body ID to an image server, wherein the image server comprises a non-transitory radiation image storage medium configured to store diagnostic data and a non-transitory optical image storage medium, configured to store body image data;
  acquire at least one optical image of said body assigned with said body ID from the image server, wherein the image server searches for said optical image of said body by using said body ID from the non-transitory optical image storage medium;
  perform display processing to display said at least one optical image of said body in a user page on said display device;
  acquire said radiation image of said body from the image server, wherein the image server searches for said radiation image of said body by using said body ID from the non-transitory radiation image storage medium; and
  perform display processing to display said radiation image of said body in said user page on said display device, wherein a size of said displayed optical image is larger than that of said displayed radiation image in said user page.

2. A console device as defined in claim 1, wherein said display device includes a touchscreen display device having a longer side equal to or less than 260 mm and a shorter side equal to or less than 180 mm, in a faun of a tablet terminal device.

3. A console device as defined in claim 1, wherein said processor displays said radiation image in a reduced size in said user page;
 when said radiation image is selected in said user page, said processor changes over said display device from said user page to a view page, and causes said view page to display said radiation image in an enlarged size.

4. A console device as defined in claim 1, wherein said processor outputs said user page in a scrollable manner, and in case said user page with said optical image is scrolled, performs display control to display said optical image in said user page even after scrolling.

5. A console device as defined in claim 1, wherein in case plural optical images are acquired, at least one first optical image among said optical images is displayed in said user page.

6. A console device as defined in claim 2, wherein said processor further causes said user page to display said radiation image in a first user menu and said optical image of said body in a list form in a second user menu.

7. A console device as defined in claim 2, wherein said processor deletes a margin portion disposed around said body in said radiation image, to display a modified radiation image formed by deleting said margin portion.

8. A console device as defined in claim 6, wherein alphanumeric information is displayed in at least one portion of said first or second user menu, and has a height equal to or more than 5 mm and a width equal to or more than 5 mm.

9. A console device as defined in claim 6, wherein the processor receives said body ID for recognition of said body in response to an input of ID detected by the touchscreen display device.

10. A console device as defined in claim 8, wherein said processor arranges and displays said first user menu adjacently with said radiation image in a display area of a size equal to said optical image.

11. A console device as defined in claim 9, said body ID is displayed in said user page.

12. A console device as defined in claim 9, wherein the processor further actuates an optical camera in said tablet terminal device when image acquisition is instructed in said second user menu, and for acquiring said optical image from said optical camera.

13. A console device as defined in claim 9,
wherein the processor further searches for a past radiation image from said radiation image storage medium according to said body ID input,
wherein when said past radiation image is found to exist, then said processor displays information of existence of said past radiation image in said user page.

14. A console device as defined in claim 12, wherein said processor displays said optical image from said non-transitory optical image storage medium in said user page;
when a new optical image is acquired from said optical camera, said processor updates said user page to display said new optical image in place of said optical image.

15. A console device as defined in claim 3, wherein when said display device is changed over from said view page to said user page, said processor causes said user page to display said radiation image displayed in said view page.

16. A console device as defined in claim 5, wherein said processor displays information of existence of an undisplayed optical image among said plural optical images in an overlapped manner with said first optical image.

17. A control method for a portable information terminal device for acquiring a radiation image of a body created by a radiographic imaging device, comprising steps of:
transmitting a body ID to an image server, wherein the image server comprises a non-transitory radiation image storage medium configured to store diagnostic data and a non-transitory optical image storage medium, configured to store body image data;
acquiring at least one optical image of said body assigned with said body ID from the image server, wherein the image server searches for said optical image of said body by using said body ID from the non-transitory optical image storage medium;
performing display processing to display said at least one optical image of said body in a user page on said display device;
acquiring said radiation image of said body from the image server, wherein the image server searches for said radiation image of said body by using said body ID from the non-transitory radiation image storage medium; and
performing display processing to display said radiation image of said body in said user page on said display device, wherein a size of said displayed optical image is larger than that of said displayed radiation image in said user page.

18. A radiographic imaging system comprising:
a radiographic imaging device for creating a radiation image of a body;
a console device of a portable type for acquiring said radiation image; and
a console holder for holding said console device;
said console device including a processor configured to:
transmit a body ID to an image server, wherein the image server comprises a non-transitory radiation image storage medium configured to store diagnostic data and a non-transitory optical image storage medium, configured to store body image data;
acquire at least one optical image of said body assigned with said body ID from the image server, wherein the image server searches for said optical image of said body by using said body ID from the non-transitory optical image storage medium;
perform display processing to display said at least one optical image of said body in a user page on said display device;
acquire said radiation image of said body from the image server, wherein the image server searches for said radiation image of said body by using said body ID from the non-transitory radiation image storage medium; and
perform display processing to display said radiation image of said body in said user page on said display device, wherein a size of said displayed optical image is larger than that of said displayed radiation image in said user page.

* * * * *